(12) United States Patent
Langheier et al.

(10) Patent No.: US 10,706,128 B2
(45) Date of Patent: Jul. 7, 2020

(54) SYSTEM AND METHOD FOR AUTOMATED PERSONALIZED AND COMMUNITY-SPECIFIC EATING AND ACTIVITY PLANNING, LINKED TO TRACKING SYSTEM WITH AUTOMATED MULTIMODAL ITEM IDENTIFICATION AND SIZE ESTIMATION SYSTEM

(75) Inventors: Jason Langheier, San Francisco, CA (US); David Kim Tcheng, Champaign, IL (US)

(73) Assignee: Zipongo, San Francisco, CA (US)

( * ) Notice: Subject to any disclaimer, the term of this patent is extended or adjusted under 35 U.S.C. 154(b) by 244 days.

(21) Appl. No.: 13/106,845

(22) Filed: May 12, 2011

(65) Prior Publication Data
US 2012/0094258 A1    Apr. 19, 2012

Related U.S. Application Data

(60) Provisional application No. 61/334,113, filed on May 12, 2010, provisional application No. 61/334,108, filed on May 12, 2010.

(51) Int. Cl.
    *G06F 19/00*    (2018.01)
    *G16H 40/63*    (2018.01)
(52) U.S. Cl.
    CPC ...... *G06F 19/3475* (2013.01); *G06F 19/3481* (2013.01); *G16H 40/63* (2018.01)
(58) Field of Classification Search
    CPC . G06Q 30/02; G06F 19/3475; G06F 19/3481; G06F 17/30247; G09B 19/0092; G09B 19/00; G09B 5/00

USPC .......................................... 434/127; 128/921
See application file for complete search history.

(56) References Cited

U.S. PATENT DOCUMENTS

| | | | |
|---|---|---|---|
| 8,363,913 B2* | 1/2013 | Boushey et al. | 382/128 |
| 2002/0047867 A1* | 4/2002 | Mault et al. | 345/810 |
| 2002/0156351 A1 | 10/2002 | Sagel | |
| 2005/0049920 A1 | 3/2005 | Day et al. | |
| 2005/0113649 A1* | 5/2005 | Bergantino | 600/300 |
| 2005/0113650 A1 | 5/2005 | Pacione et al. | |
| 2007/0190501 A1* | 8/2007 | Brown et al. | 434/127 |
| 2008/0083825 A1* | 4/2008 | Yang et al. | 235/375 |
| 2008/0300109 A1 | 12/2008 | Karkanias et al. | |
| 2009/0312998 A1 | 12/2009 | Berckmans et al. | |
| 2011/0172497 A1 | 7/2011 | Ruby et al. | |

OTHER PUBLICATIONS

International Search Report, PCT/US11/36362, dated Aug. 11, 2011.
Written Opinion, PCT/US11/36362, dated Aug. 11, 2011.

* cited by examiner

*Primary Examiner* — Jerry-Daryl Fletcher
(74) *Attorney, Agent, or Firm* — DLA Piper LLP (US)

(57) ABSTRACT

The system and method for automated personalized and community-specific eating and activity planning are provided that are linked to tracking with automated multimodal item identification and size estimation and enable and integrate health and other user datastreams and enables rewards and links to healthy eating and activity partners based on that data. The system and method also provide personalized wellness recommendations. The system and method also enables action, such as single click ordering of the healthy meals or shopping list on one's plan from local restaurants and grocery stores, and receipt of mobile vouchers and coupons with a unique validation system for use at retailers.

22 Claims, 36 Drawing Sheets

2 FOR 1 PUBLIC SKATING OFFER

FIG. 7

| HOME | FITNESS MANAGER | FOOD MANAGER | USER MANAGER | INSTITUTION MANAGER | INDICATORS MANAGER |

HELLO

MY ADMIN
- GENERAL FOOD
- FOOD PLANS
- FOOD INGREDIENTS

MY CALENDAR
- MY DAY
- MY WEEK
- MY MONTH
- MY FAVORITES

GENERAL FOOD

| BUTTER, SALTED | MODIFY | DELETE |
| BUTTER, WHIPPED, WITH SALT | MODIFY | DELETE |
| BUTTER OIL, ANHYDROUS | MODIFY | DELETE |
| CHEESE, BLUE | MODIFY | DELETE |
| CHEESE, BRICK | MODIFY | DELETE |
| CHEESE, BRIE | MODIFY | DELETE |
| CHEESE, CAMEMBERT | MODIFY | DELETE |
| CHEESE, CARAWAY | MODIFY | DELETE |
| CHEESE, CHEDDAR | MODIFY | DELETE |
| CHEESE, CRACKERS | MODIFY | DELETE |
| CHEESE, CAKE | MODIFY | DELETE |
| CHEESE, COTTAGE, CREAMED, LARGE OR SMALL CURD | MODIFY | DELETE |
| CHEESE, COTTAGE, CREAMED WITH FRUIT | MODIFY | DELETE |
| CHEESE, COTTAGE, LOWFAT, 2% MILKFAT | MODIFY | DELETE |
| CHEESE, COTTAGE, LOWFAT, 1% MILKFAT | MODIFY | DELETE |
| CHEESE, CREAM | MODIFY | DELETE |
| CHEESE, FETA | MODIFY | DELETE |
| CHEESE, FONTINA | MODIFY | DELETE |
| CHEESE, GRUYERE | MODIFY | DELETE |

ALL A B C D E F G H I J K L M N O P Q R S T U V W X Y Z
1 2 3 4 5 6 7 8 9 10
FOOD FOR ME [GO!] [RESET]

ADD FOOD

NAME: _____
MANUFACTURER NAME (IF IT IS A BRAND NAME): _____
GROUP: BABY FOODS ▼
AMOUNT: $ ____
MEASURE DESCRIPTION: _____
GRAMS WEIGHT: 0.00
HEALTHY FOOD: ☐
USDA CODE (FOR NUTRITION INFO): _____

[ADD FOOD]

| HOME | FITNESS MANAGER | FOOD MANAGER | USER MANAGER | INSTITUTION MANAGER | INDICATORS MANAGER |

| ACTIVITY TYPE | ACTIVITY SUBTYPE |

HELLO

MY ADMIN
○ FITNESS PLACES
○ FITNESS ACTIVITIES
○
○

MY CALENDAR
○ MY DAY
○ MY WEEK
○ MY MONTH
○ MY FAVORITES

FITNESS ACTIVITIES

| NAME | ACTIVITY TYPE | ACTIVITY | | |
|---|---|---|---|---|
| AQUATIC VOLLEYBALL | AEROBIC | AEROBICS | MODIFY | DELETE |
| BALL AEROBICS | AEROBIC | AEROBICS | MODIFY | DELETE |
| BODYSTYLING | AEROBIC | AEROBICS | MODIFY | DELETE |
| BREATH AEROBICS | AEROBIC | AEROBICS | MODIFY | DELETE |
| CIRCUIT TRAINING AEROBICS | AEROBIC | AEROBICS | MODIFY | DELETE |
| DANCE AEROBICS | AEROBIC | AEROBICS | MODIFY | DELETE |
| HYLO AEROBICS | AEROBIC | AEROBICS | MODIFY | DELETE |
| INTERVAL AEROBICS | AEROBIC | AEROBICS | MODIFY | DELETE |
| KICKBOXING AEROBICS | AEROBIC | AEROBICS | MODIFY | DELETE |
| STEP AEROBICS | AEROBIC | AEROBICS | MODIFY | DELETE |
| STEP/INTERVAL AEROBICS | AEROBIC | AEROBICS | MODIFY | DELETE |
| TAEKO | AEROBIC | AEROBICS | MODIFY | DELETE |
| TAIBO | AEROBIC | AEROBICS | MODIFY | DELETE |
| AEROBICS | AEROBIC | AEROBICS | WATER AEROBICS | MODIFY DELETE |
| BODY BOARD | AEROBIC | WATER SPORTS | MODIFY | DELETE |
| BOOGIE BOARD | AEROBIC | WATER SPORTS | MODIFY | DELETE |
| PARASAILING | AEROBIC | WATER SPORTS | MODIFY | DELETE |
| SURFING | AEROBIC | WATER SPORTS | MODIFY | DELETE |
| WINDSURFING | AEROBIC | WATER SPORTS | MODIFY | DELETE |
| WATERSKIING | AEROBIC | WATER SPORTS | MODIFY | DELETE |

ALL A B C D E F G H I J K L M N O P Q R S T U V W X Y Z 1 2 3 4 5 6 7 8 9 10

ACTIVITY: [ GO! ] [ RESET ]

ADD ACTIVITY

NAME: [                    ]
ACTIVITY SUB-TYPE: [ SELECT AN ACTIVITY SUBTYPE ▼ ]
SYNONYM: [                    ]

[ ADD ACTIVITY ]

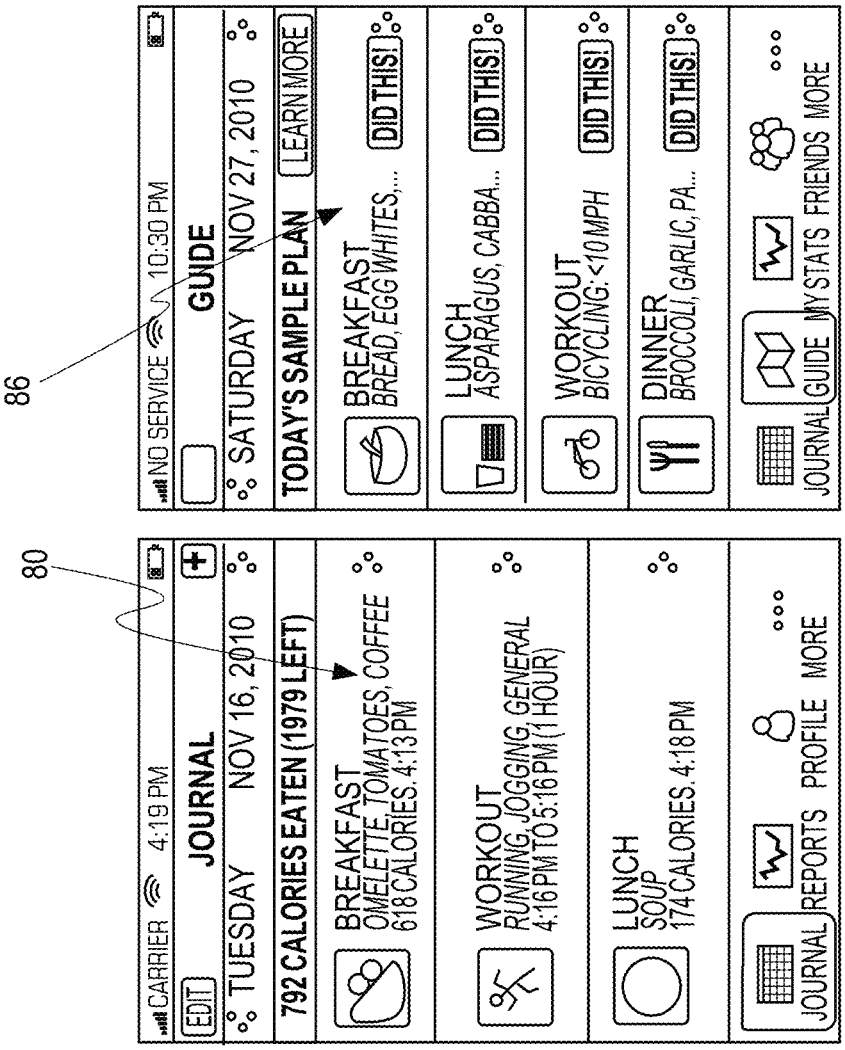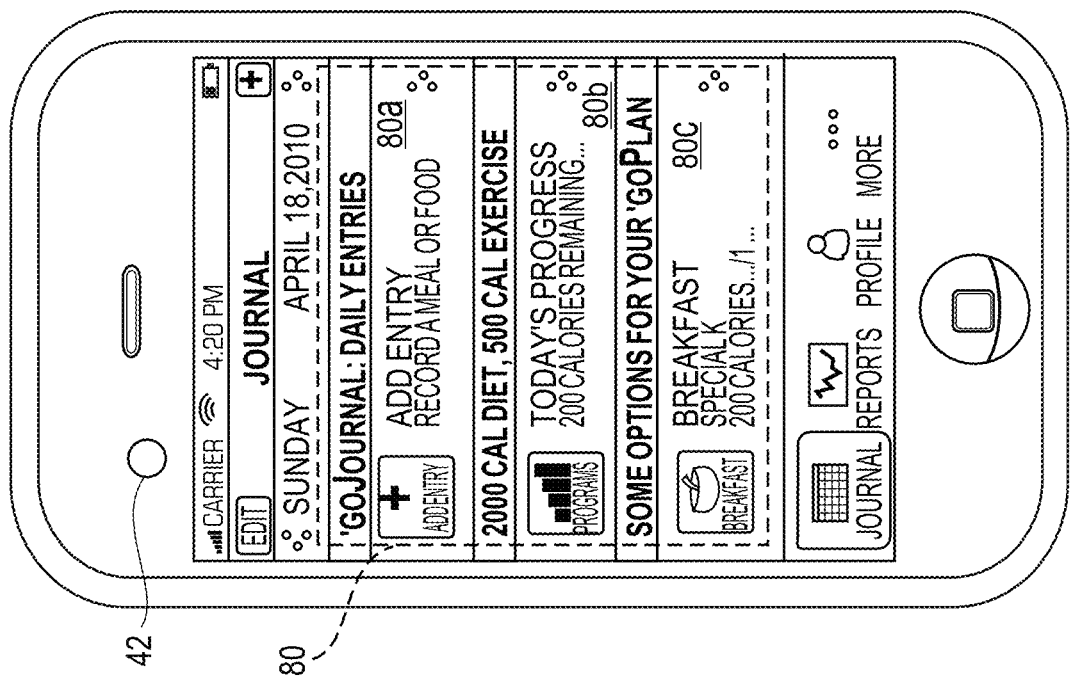

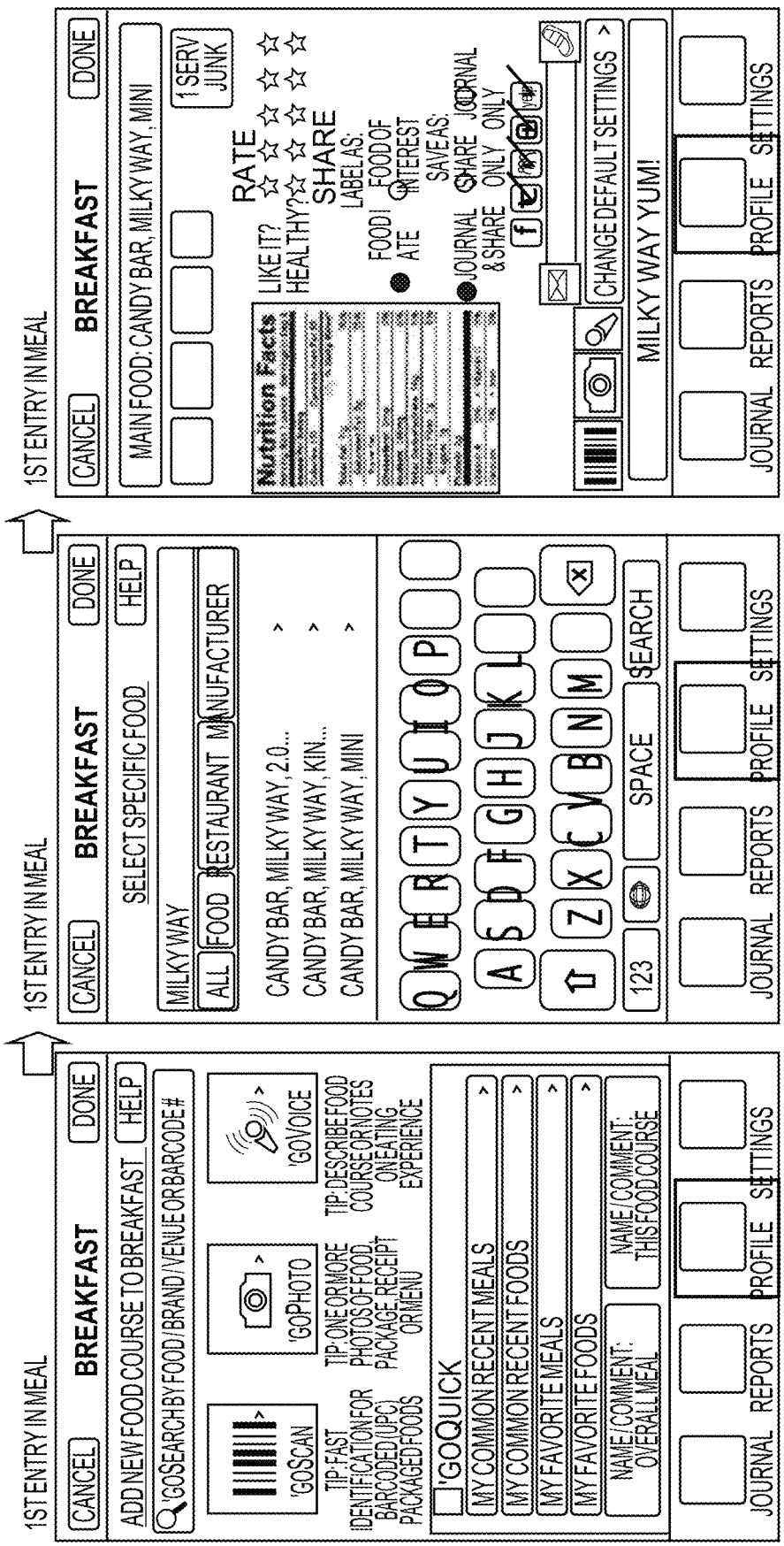

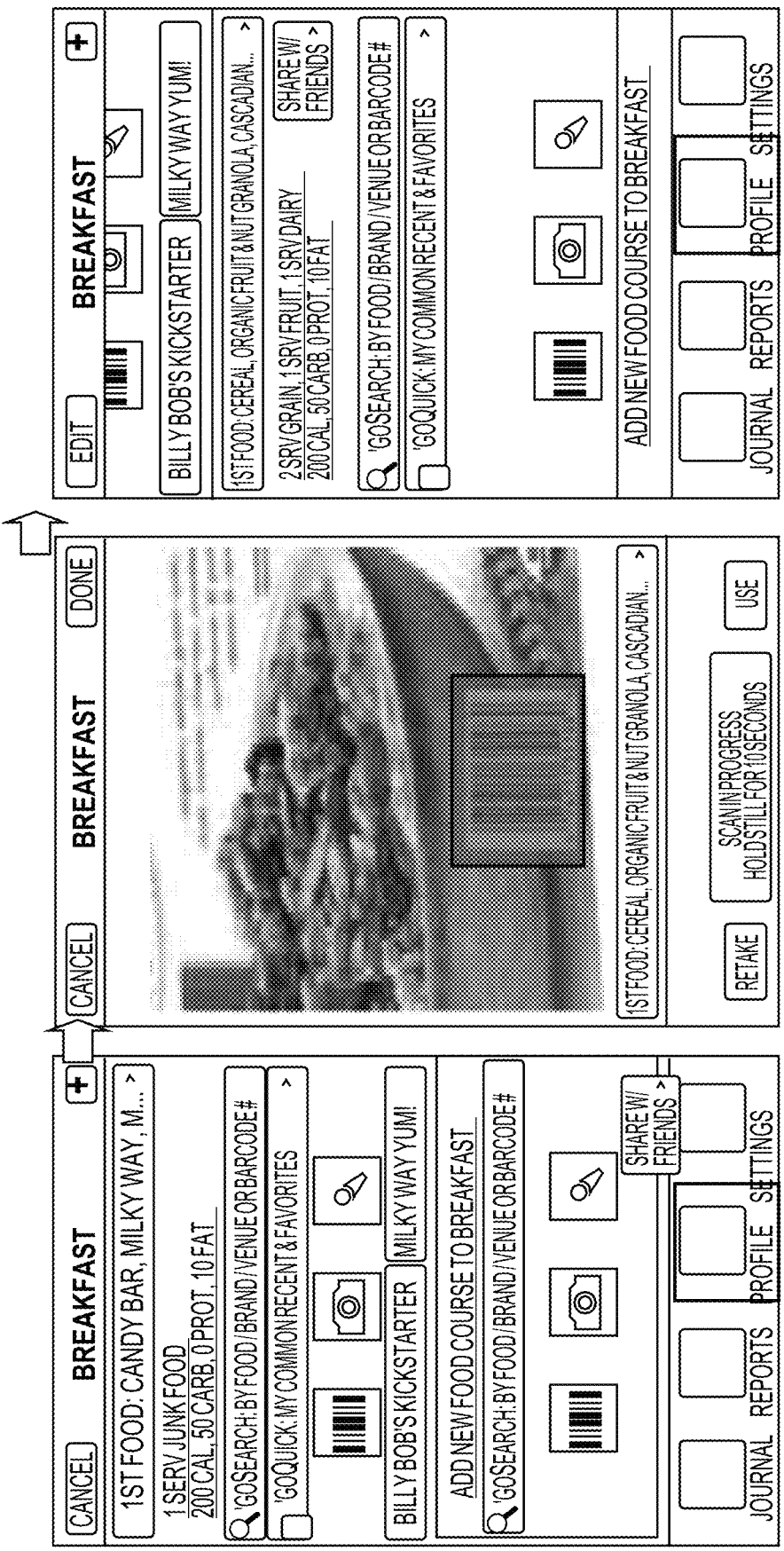

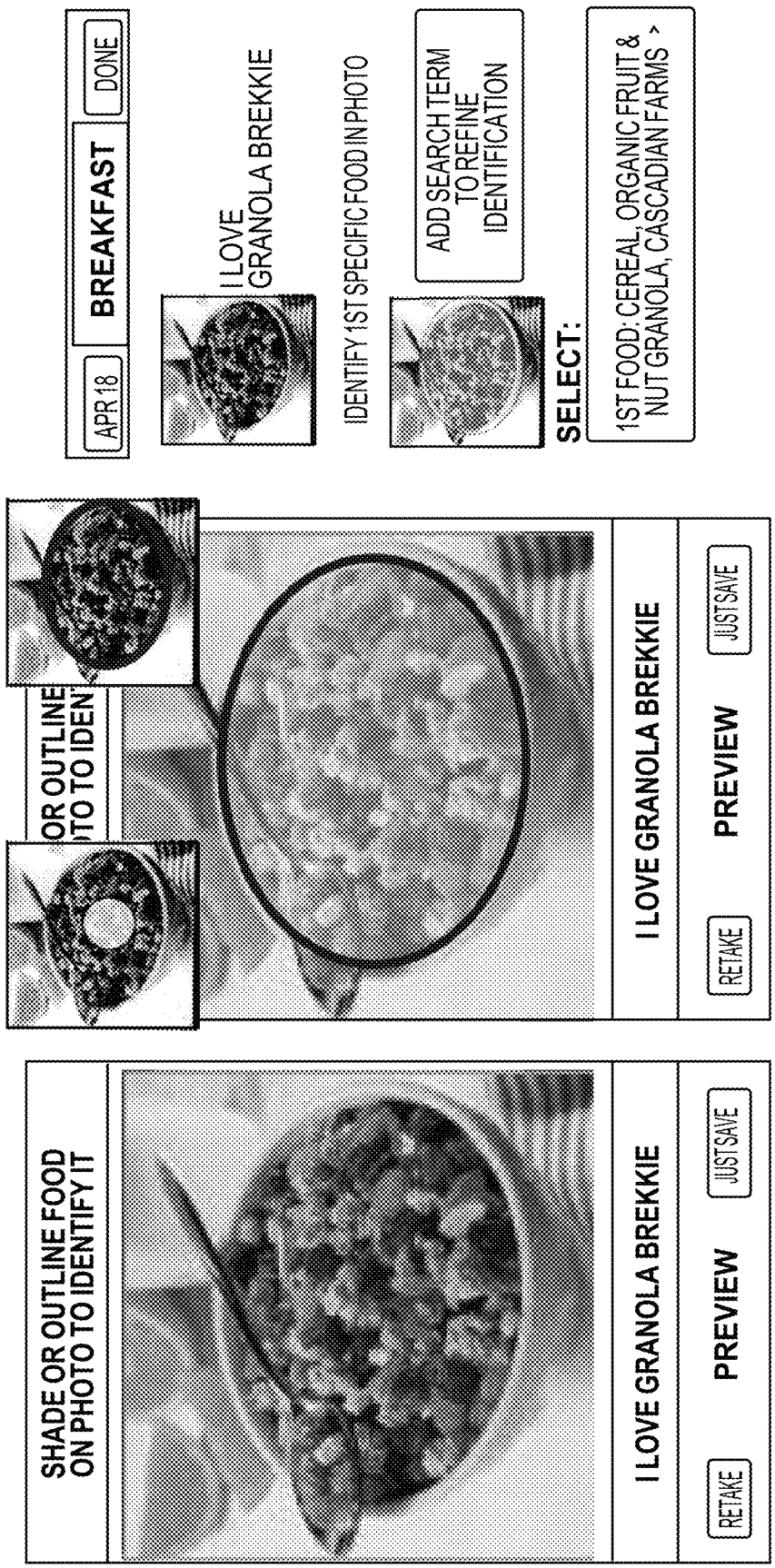

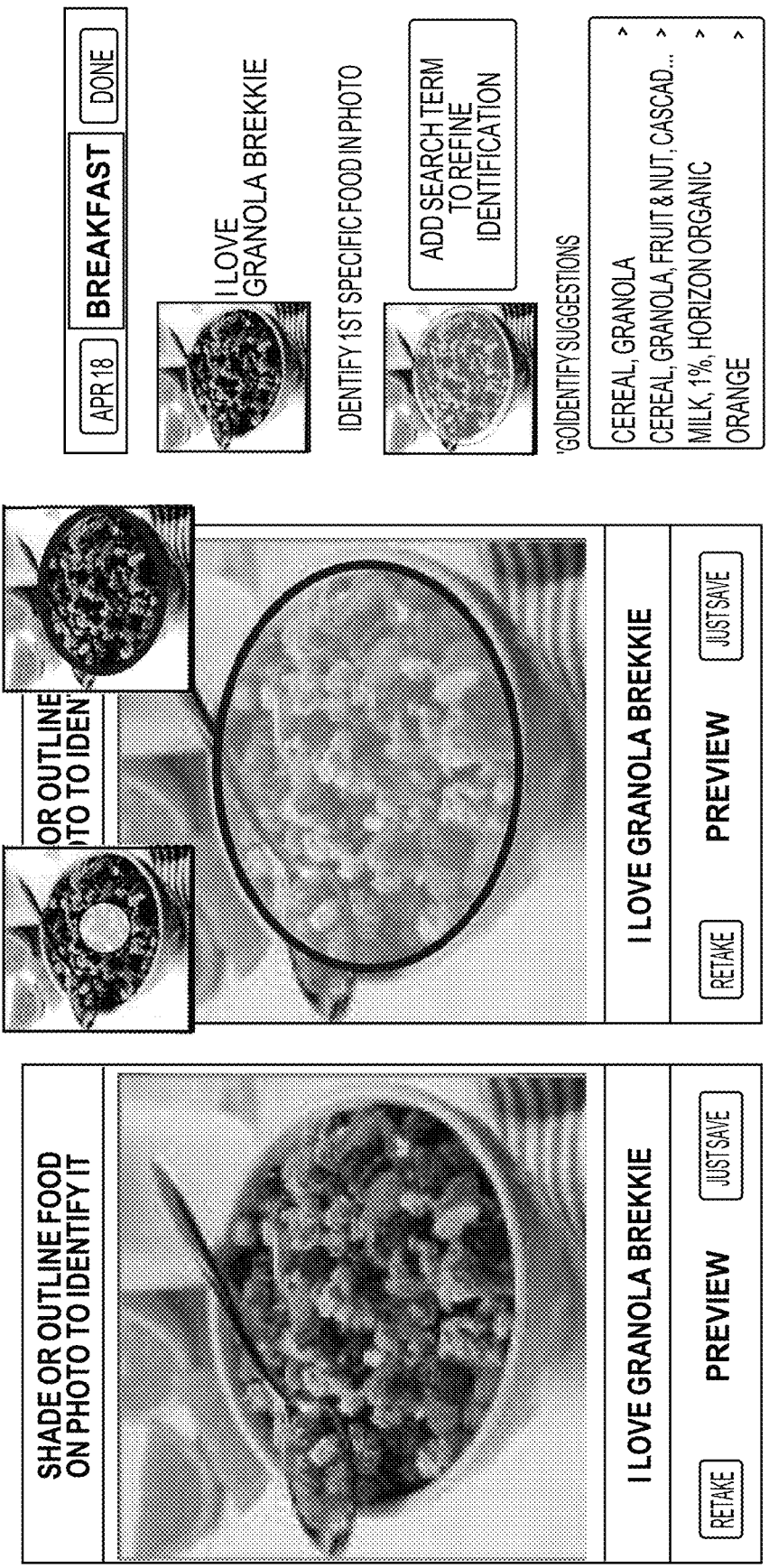

SYSTEM AND METHOD FOR AUTOMATED PERSONALIZED AND COMMUNITY-SPECIFIC EATING AND ACTIVITY PLANNING, LINKED TO TRACKING SYSTEM WITH AUTOMATED MULTIMODAL ITEM IDENTIFICATION AND SIZE ESTIMATION SYSTEM

FIELD

This application claims the benefit under 35 USC 119(e) and 120 to U.S. Provisional Patent Application Ser. No. 61/334,113, filed on May 12, 2010 and titled "Optimization Of Eating, Physical Activity And Other Lifestyle Tracking Through Integration Of Data Capture Methods And Predictive Modeling For Prioritized Item Search And Suggestions To User" and claims the benefit under 35 USC 119(e) and 120 to U.S. Provisional Patent Application Ser. No. 61/334, 108, filed on May 12, 2010 and titled "Collaborative Filtering And Search Methods For Recommending An Optimal Food, Exercise And Other Lifestyle Behaviors Based On A Person's Characteristics, Health Risks, Preferences, Location, Budget, Social Network And Other Factors", the entirety of both of which are incorporated herein by reference.

BACKGROUND

Tracking what a person eats in a more automated way, through the combination of visual recognition, voice recognition, GPS information, mechanical turk, data feed integration, and a simplified user interface, could revolutionize the awareness of people, improving the consistency with which more of us understand how and what we eat. The significance and magnitude of health issues related to nutrition and other health behaviors are now, relatively well known. Caloric over-consumption, poor nutritional balance and lack of physical activity are primary drivers of negative health outcomes in modernized nations. The Centers for Disease Control and Prevention (CDC) says these behaviors together were the #2 'actual cause of death' in 2000 (365,000 deaths, 15.2% of total), narrowly behind smoking; these behaviors far outpace alcohol, infection, toxins, accidents, firearms, unsafe sexual behavior and illicit drug use as causes of death. Poor diet and physical inactivity are major contributors to obesity, which may have cost the United States as much as $78.5 B in direct medical expenses in 1998 (1998 dollars), nearly 10% of healthcare spending, not including indirect expenses. Obesity is expected to halt American's rise in life expectancy in the first half of this century. Even today, US life expectancy is ranked only 45th (30th among UN member nations) in the world (78.06 years at birth), despite spending the most on healthcare in total ($1.5 T or 14.9% GDP in 2003; $3.7 T expected by 2013) 10 and per capita ($4887). Poor diet, physical activity, and obesity itself, are all risk factors for the development of cancer, diabetes and cardiovascular disease, among other chronic conditions. In 2005, cancer and chronic disease accounted for approximately 70% of the giant US healthcare price tag, with cardiovascular disease accounting for 17%, cancers for 7% and diabetes for 4% (obesity not listed separately). In a separate US study on 2005 data, 44% of people surveyed had at least one chronic disease, and individual out-of-pocket spending went up 39% to an average of $741/year.

We see accurate, consistent and widely adopted health behavior tracking and planning as critical to individual and cultural awareness building for adoption healthy behaviors; understanding what one eats or how they engage in consistent physical activity, will be fundamental to overcome obesity and chronic disease. It is desirable to provide tracking tools to help overcome these health challenges.

Existing tracking systems/products do not allow a user to capture food images and provide automated and non-human annotation services to help codify the data. Further, few of the currently available tools have dramatically altered behavior or clinical outcomes on a population level, though a recent study showed 58% of patients across age groups look up health information on the web currently. A number of web-based tools and some simple mobile applications exist in the marketplace to help people to plan a diet, or an exercise routine, typically from the perspective of helping people to lose weight. The commercial argument for the obesity emphasis is that a fraction of the large population of overweight patients are contemplating change or already motivated (in Preparation stage) to lose weight for health reasons or aesthetics. Most use subscription models for which motivated consumers are willing to pay, and a few rely on advertising revenue.

But, no effective tools have been developed to accurately help people quantitatively, accurately and consistently track their dietary intake, which people are also pleased to use on an ongoing basis. Self-report food frequency questionnaires are notoriously inaccurate, and food journals are accurate if items are tracked at the time of consumption, but very few people will continue to take the time or even want to focus on this level of detail about what they eat, for more than a period of a couple of weeks. It is desirable to provide a product/system that addresses these issues.

Caloric overconsumption, lack of physical activity and inadequate sleep are three of the primary drivers of negative health outcomes in modernized nations. All three contribute to obesity, which cost the United States between 70 and 100 billion dollars in direct medical costs alone, and is expected to halt American's rise in life expectancy in the first half of this century. Obesity and each of these three health habits are risk factors for the development of heart disease, cancer, stroke, type 2 diabetes, and osteoporosis, among other conditions. Unfortunately, recommendations to be active, eat smart and sleep well are typically impersonal, generic, non-actionable, incompatible with daily commitments, unnecessarily expensive, easily forgotten and are far less frequent than competing messages promoting unhealthy nutrition and sedentary activities. Further, the availability of affordable and comprehensive services that promote long-lasting changes in behavior and body weight is low, creating a need for innovative solutions.

Thus, it is desirable to provide a system and method for automated personalized and community-specific eating and activity planning, linked to tracking with automated multimodal item identification and size estimation that overcomes the limitations of the above existing systems and method and it is to this end that the disclosure is directed.

BRIEF DESCRIPTION OF THE DRAWINGS

Figure 9:
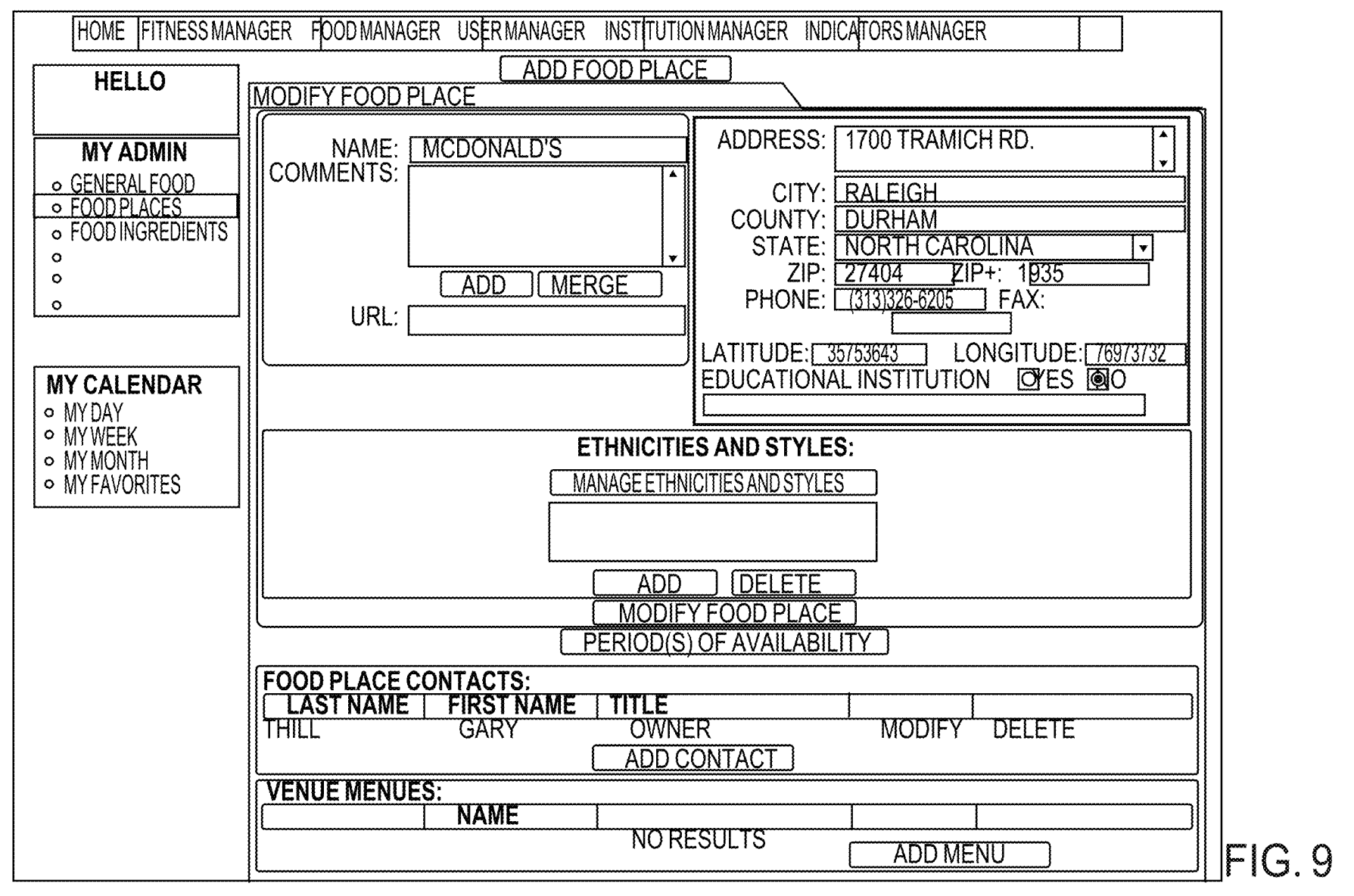
Figure 10:
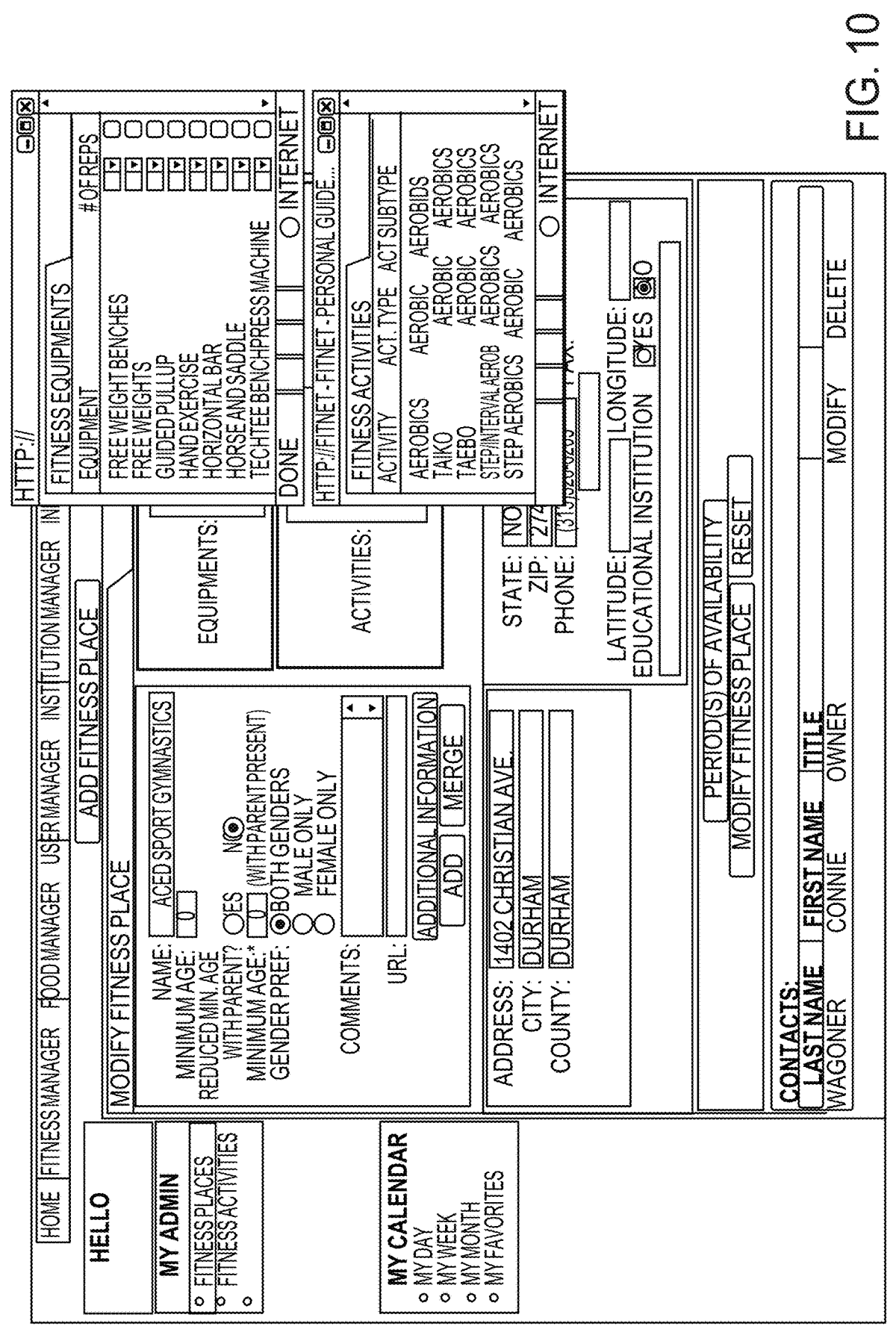

FIGS. 7-10 illustrate examples of other user interface of the FitNet website that is part of the community-specific and personalized nutrition and activity planning system;

FIGS. 19A and 19B illustrate an example of a journal user interface of the computing device app;

FIG. 19C illustrates an example of a guide user interface of the computing device app;

FIG. 26 illustrates an example of an automatically generated grocery list of the computing device app;

FIG. 27 illustrates an example of food information user interface of the computing device app;

FIGS. 29A-C illustrate examples of a breakfast, lunch and dinner user interface of the computing device app;

FIGS. 30A-C illustrate examples of a barcode/UPC scanning process using the computing device app;

FIGS. 32A-C illustrate examples of a meal capture image process with prior barcode scanning using the computing device app;

FIGS. 33A-C illustrate examples of a meal capture image process without prior barcode scanning using the computing device app;

Figure 36A:
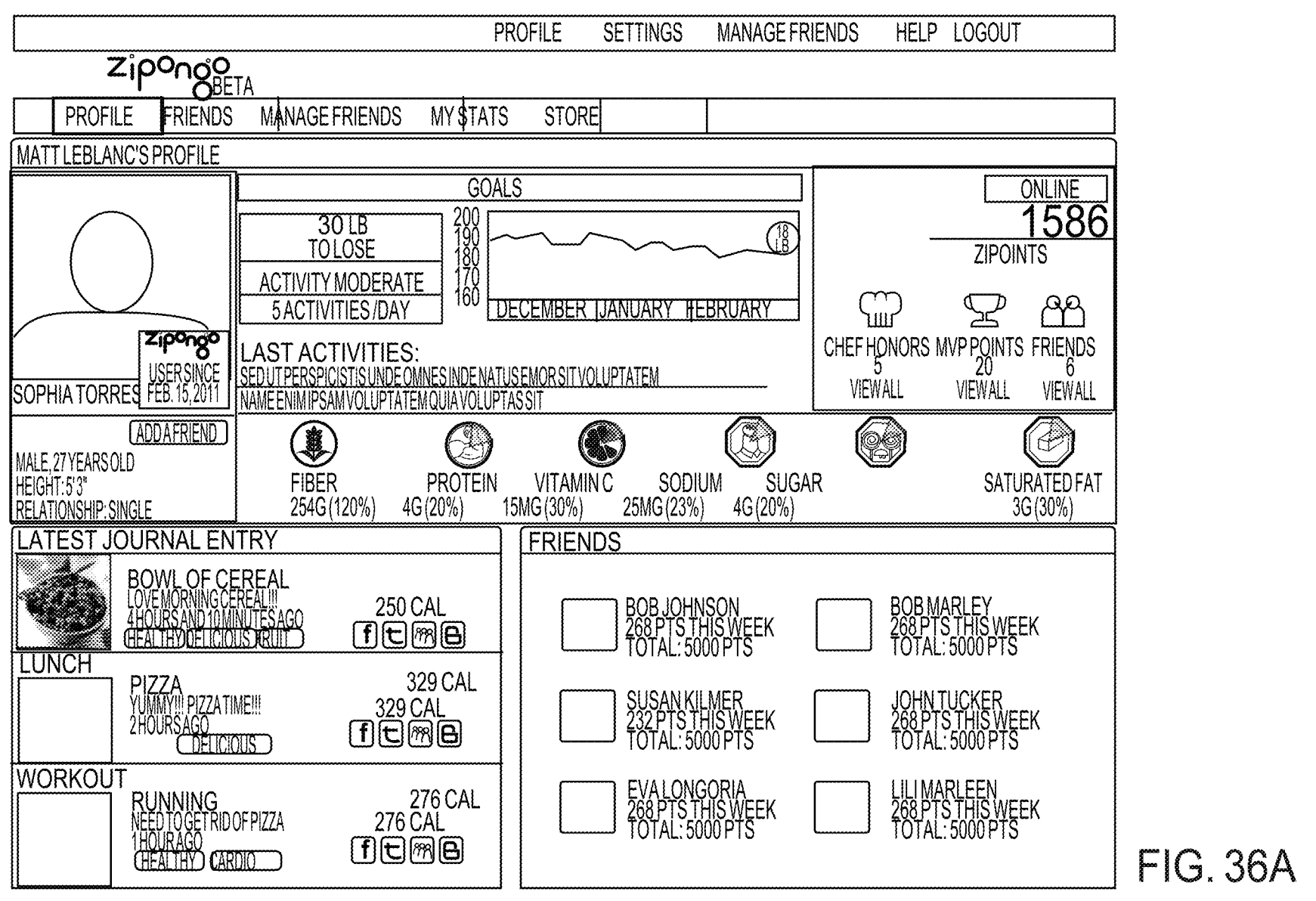
Figures 36C, 36D:
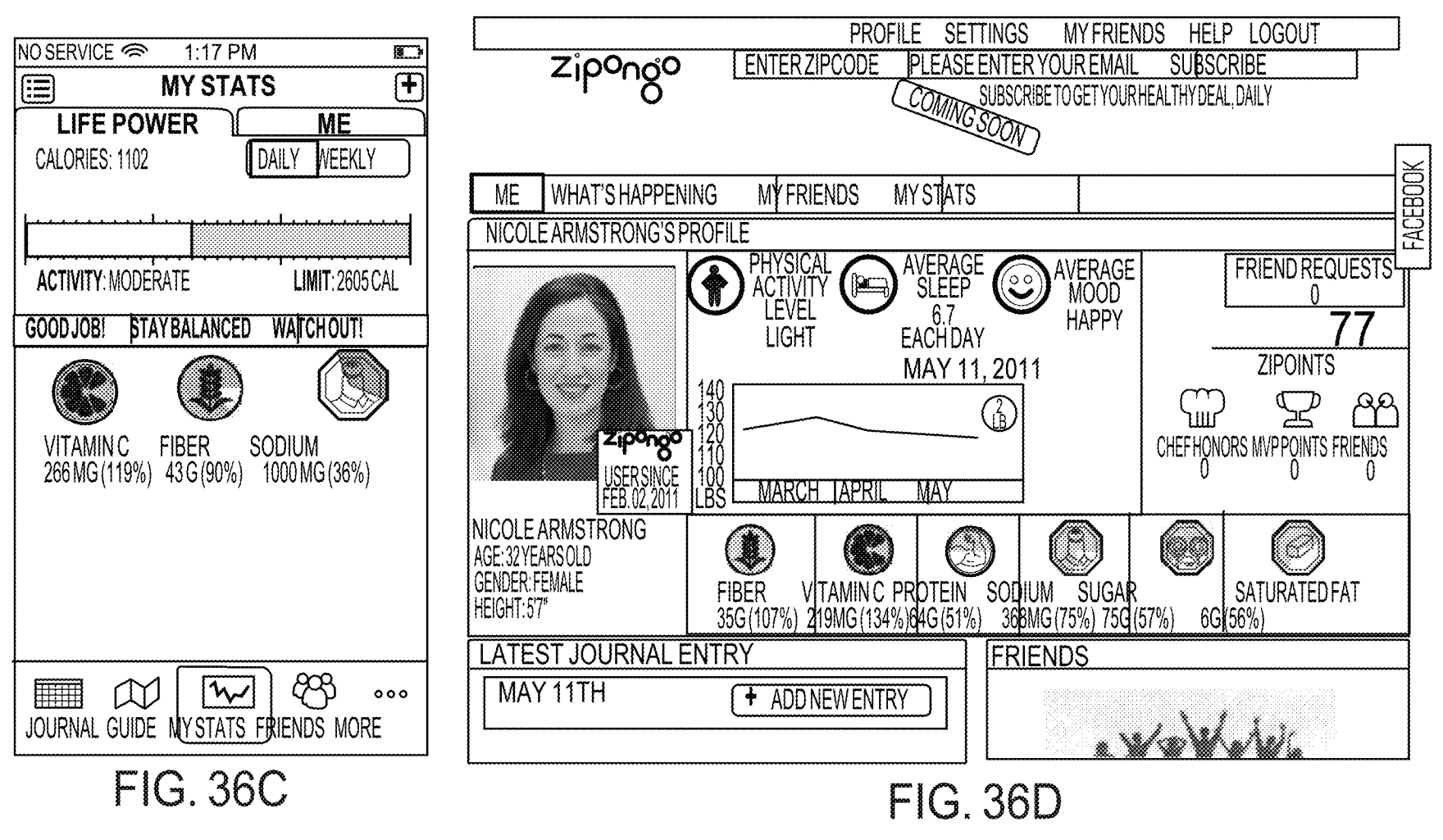

FIGS. 36A-D illustrate examples of LifePower user interfaces for the community-specific and personalized nutrition and activity planning system;

DETAILED DESCRIPTION OF ONE OR MORE EMBODIMENTS

Figure 1:
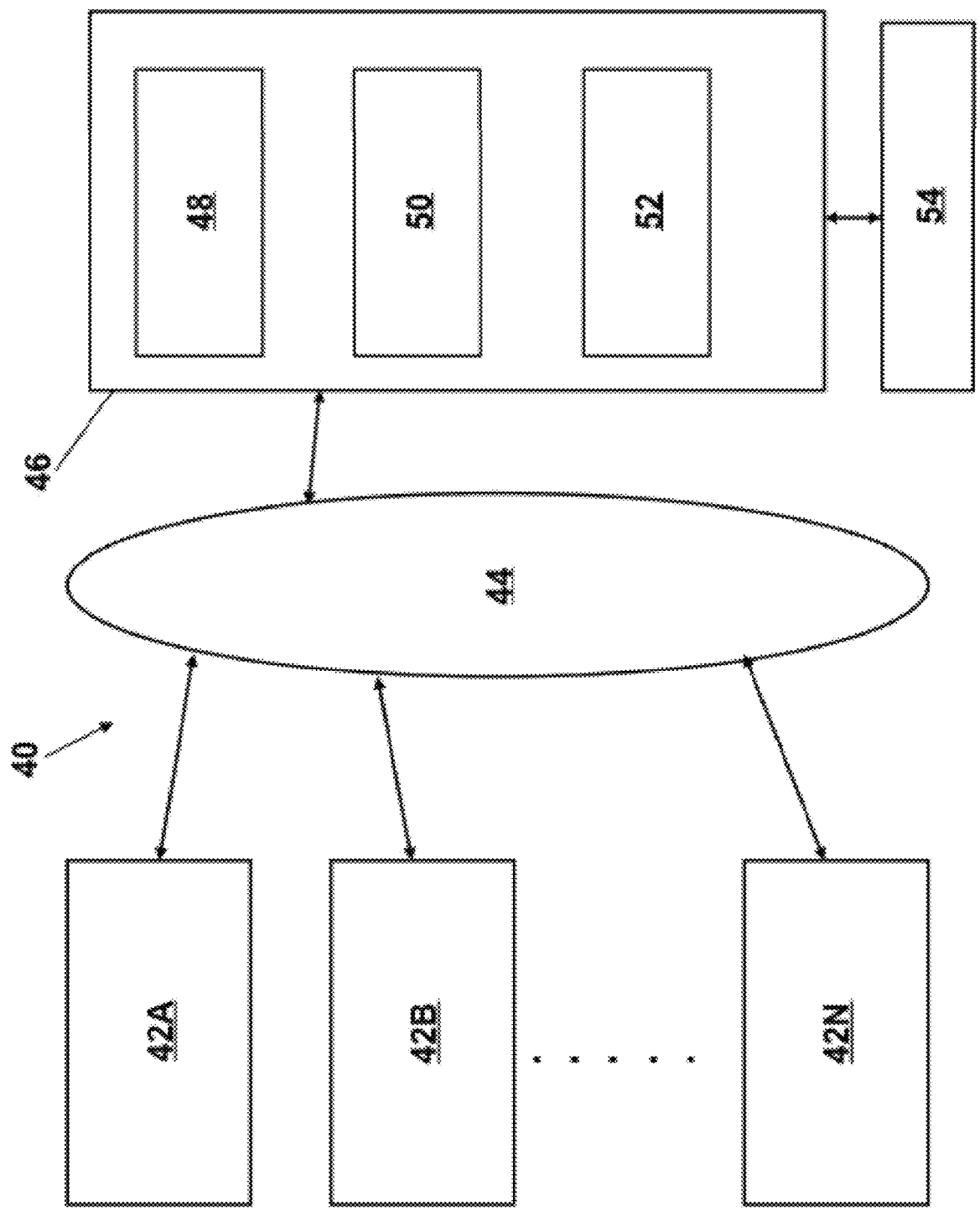
FIG. 1 illustrates an example of a mobile device based implementation of a community-specific and personalized nutrition and activity planning system.

The disclosure is particularly applicable to a mobile and web-based device implementation of a system and method for automated personalized and community-specific eating and activity planning, linked to tracking with automated multimodal item identification and size estimation, and it is in this context that the disclosure will be described. It will be appreciated, however, that the system and method in accordance with the disclosure has greater utility since it can be implemented using other computer architectures, other computing devices than those disclosed below and may have a different user interface than the examples below, but is within the scope of the disclosure.

The system and method for automated personalized and community-specific eating and activity planning, linked to tracking with automated multimodal item identification and size estimation, enables and integrates health and other user datastreams, enables rewards and links to healthy eating and activity partners based on that data—both external and internal. The system and method also provide personalized wellness recommendations for eating, physical activity, sleep, stress reduction and other elements of daily living, tailored to each user based on the preferences, prior history, location and budget information provided by the users. Data inputs for elements such as food tracking are made simpler and more accurate through multimodal recognition combining database subsetting based on geolocation user check-ins based on global positioning system recommendations (such as checking into a restaurant and subsetting to a menu), voice recordings interpreted to text by existing voice recognition algorithms, descriptive text entered by users tracking the food or other item of interest, or other humans through services such as mechanical turk, together with any of a number of available image visual recognition tools using pixel level color and texture (pixel comparison) analysis plus instance based and classification and regression tree algorithms. The system and method also enables action, such as single click ordering of the healthy meals or shopping list on one's plan from local restaurants and grocery stores, and receipt of mobile vouchers and coupons with a unique validation system for use at retailers. Once foods are bought, scanning of unique barcodes and multimodal item recognition from FitNet can also be used for tracking and management of a user's pantry and food at home.

The system and method also facilitate key processes of change along the stages of change articulated by the Transtheoretical Model (TTM), which has underlying roots in Social Cognitive and Motivational Theories. Unlike known system that 1) lack tools that are both simple, fast and accurate in providing consistent behavioral feedback and awareness, and 2) they do not effectively span the complete Stages of Change process, allowing people to relapse after initial success, the system provides tools that are both simple, fast and accurate in providing consistent behavioral feedback and awareness for nutritional tracking.

Except during sporadic periods where people are placed in controlled nutritional environments, truly knowing what you eat is a necessary first step to consistently adopting and maintaining healthy eating behaviors. The system provides a faster, easier and thus more consistent use, more accurate tracking and more valuable feedback, trends analysis and correlations related to nutrition, physical activity, stress and energy level. Among Social or "Foodie" users, there is an added value proposition of being able to easily share information about one's life with friends, family and social network, which can help to engage a larger population, beyond those simply drawn to the health and fitness aspects of the system.

The system may be implemented as a mobile device based and web-based system for capturing, codifying, tracking and sharing information about the foods the user sees, the meals the user eats and the food venues the user visits. The system also has the personalized wellness planning and recommendation web-application, and syndicate to existing popular social networking and productivity tools.

The mobile device of the system can be a transformative tool for improving health behavior and the accuracy of epidemiologic research. The components of the mobile device (and the application/program running on the mobile device) may include: 1) image capture of a meal and optionally, its dimensions (i.e. width and height of a glass) and added data such as menu description, food labels or receipts, leveraging mobile phone cameras; 2) user image annotation, involving quick, simple and optional user data entry (name of meal, component foods, length of time spent, rating overall/taste/convenience/price/perceived healthfulness/ambience of venue), tagging or voice annotation or additional pictures of receipt, menu and/or nutrient label pictures; 3) the recommendation image annotations and analysis, including both automated features such as GPS tagging and naming of the user's current location, interpretation of barcode images and matching with our food product database, matching restaurant foods to our restaurant food data, matching previously imaged foods to newly captured images, visual recognition software for simple foods (as used in food distribution quality assurance systems), crowdsourcing information through online quizzes that provide rewards, and finally, use of Amazon Mechanical Turk and trained staff for more challenging, non-standard images. and use of visual recognition software; 4) image tracking in a calendar and historical reports, allowing the user to review their eating history; 5) future planning in the calendar, recommending particular meals at a particular time, place and cost; and 6) social network sharing of either individual images with annotations (Facebook or Twitter update on what the user is doing), or calendar with history (past), current location (present) and plan (future), allowing others to comment on, rate, share and emulate meals, or calendar plan.

The system may be used by at least four types of users, defined by their motivational driver for using our product. These types of user include a social user, a health user, a study subject user and a convenience user.

FIG. 1 illustrates an example of a mobile device based implementation of a community-specific and personalized nutrition and activity planning system 40. The mobile device based community-specific and personalized nutrition and activity planning system may have one or more computing devices 42A-42N that communicate with and interact over a link 44 to a community-specific and personalized nutrition and activity planning unit 46. The one or more computing devices 42A-42N may each be a processing unit based device with sufficient processing power, memory capacity and wired/wireless connectivity to communicate with and interact over the link 44 to the community-specific and personalized nutrition and activity planning unit 46 as described below in more detail. For example, each computing device may be a smartphone mobile device (such as an Apple® iPhone®, a RIM® Blackberry® device, an Android operating system-based device and the like), a laptop computer, a tablet computer (such as the Apple® iPad® and the like), a Withings Body Scale (a wifi enabled scale that sends weight and body fat percentage to the internet), FitBit (movement/physical activity data through accelerometer) and Zeo (sleep tracking using EEG headband and alarm clock) and other devices that are capable of communicating with and interacting over the link 44 to the community-specific and personalized nutrition and activity planning unit 46. All of the data from these computing devices may then be integrated all in one place (and can be used to help guide prediction of items tracked and most importantly, personalized recommendations. The integrated data from the computing devices also can be used to later help predict risk of future disease and other outcomes (sleep) and help diagnose causes of symptoms (allergies, headaches, disordered sleep, etc). The link 44 may be a wireless or wired link that may be a computer network, a cellular network, a cellular digital data network, a communications network and the like. The community-specific and personalized nutrition and activity planning unit 46, in one implementation may be one or more server computers that execute a plurality of lines of code to implement the functions and operations of the community-specific and personalized nutrition and activity planning unit 46, one or more cloud based resources that execute the plurality of lines of code to implement the functions and operations of the community-specific and personalized nutrition and activity planning unit 46 or one or more hardware devices that implement the functions and operations of the community-specific and personalized nutrition and activity planning unit 46. In one embodiment, each computing device is smartphone device, the link is the Internet and the community-specific and personalized nutrition and activity planning unit 46 is one or more server computers. Although the system in FIG. 1 has a client/server type architecture, the system also may be implemented using a SaaS architecture, a cloud based architecture and the like since the system is not limited to any particular system architecture, type of computing device, type of merchant system or link.

In one implementation, each computing device may have a browser application executed by the processing unit of the computing device that is capable of communicating and interacting with the community-specific and personalized nutrition and activity planning unit 46. In other implementations, such as the illustrative one shown in FIGS. 11-25, each computing device may have an app executed by the processing unit of the computing device that is capable of communicating and interacting with the community-specific and personalized nutrition and activity planning unit 46. Each computing device may have a camera/image sensor that is used to, for example, perform an image capture of a meal and optionally, its dimensions (i.e. width and height of a glass) and an optional GPS circuit/system for determining the location of the computing device.

The community-specific and personalized nutrition and activity planning unit 46 may further comprise a web server/application programming interface (API) module 48 (that may be hardware based or software based) that receives communication/data from each computing device (whether using a browser application and web pages or an app) and sends data back to each computing device based on a request of the computing device. The web server/application programming interface (API) module 48 may also permit partners of the system, such as social networking systems, to interact with the system 40. The community-specific and personalized nutrition and activity planning unit 46 may further comprise a nutritional planning unit 50 (implemented in one embodiment as a plurality of lines of computer code executed by a processing unit of the community-specific and personalized nutrition and activity planning unit 46) that performs the nutrition planning functions, operations and processes of the system 40 that are described in more detail below. The community-specific and personalized nutrition and activity planning unit 46 may further comprise a recommendation and sharing unit 52 (implemented in one embodiment as a plurality of lines of computer code executed by a processing unit of the community-specific and personalized nutrition and activity planning unit 46) that performs the recommendation functions, operations and processes as well as the sharing functions, operations and processes that are described in more detail below. The community-specific and personalized nutrition and activity planning unit 46 may also have a store 54 (implemented in one implementation as a hardware based database or a software based database) associated with the system 40 that stores the user data of the system, the nutritional data of the system, the recommendation data of the system and the like.

Figure 2:
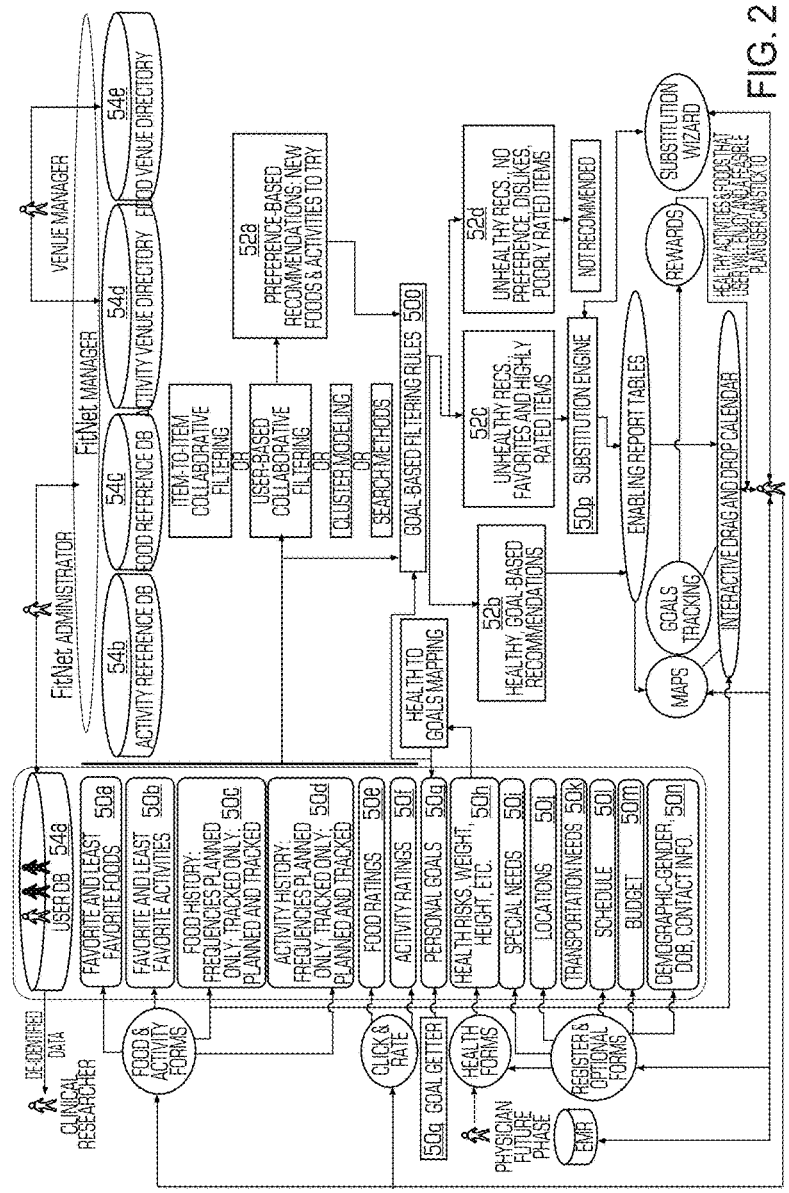
FIG. 2 illustrates more details of the community-specific and personalized nutrition and activity planning system.

FIG. 2 illustrates more details of the community-specific and personalized nutrition and activity planning system 40 and in particular more details of the nutritional planning unit 50, the recommendation and sharing unit 52 and the store 54. The store 54, in the system, may further comprise one or more databases that contain data for the system. In one implementation, the databases may a user database 54A that contains a record with data about each user, an activity reference database 54b that contains data about each activity of the community-specific and personalized nutrition and activity planning system 40 described below in more detail, a food reference database 54c that contains data about each food contained in the community-specific and personalized nutrition and activity planning system 40 described below in more detail, an activity venue database 54c that contains data about each activity venue contained in the community-specific and personalized nutrition and activity planning system 40 described below in more detail and a food venue database 54e that contains data about each food venue (e.g., restaurant, etc.) contained in the community-specific and personalized nutrition and activity planning system 40 described below in more detail. In total, the Food Reference Database contains numerous tables and relationships, including Businesses, Manufacturers. The core Food table contains food, type, subtype fields, cooking method, preparation method, storage method, derivative nutrient interpretations (i.e. low sodium, high fat, etc), manufacturer, linked retail venues, farm source and location. Ingredients, foods and recipes are all housed in the core food table. Each food is linked to a normalized recipe table that contains the component foods. Each food also links to a nutrients table that lists the nutrients for each food, and version of that food, based on source location and date of measured nutrient info—whether internal or crowdsourced and linked to a user that enters the information. Each food has derivative tags that note allergens, vegetarian status, Kosher status and other restrictions. These link to user restrictions, preference and risk tables.

In order to provide the recommendation of the system 40, the system 40 needs various user data. For new users who have not yet used the FitNet Calendar and tracked their foods and activities, the system may have a short online questionnaire that asks about food and activity preferences (favorite and least favorite foods and activities), restrictions (i.e. allergies, religious preferences, etc.), and a basic food and activity inventory for the last 2 weeks. The new user also has the option to enter budget information, transportation preferences, and other factors that affect their food, activity and venue choices. In addition, home location, age and gender information is already captured as part of basic registration for GoalGetter (described below in more detail). The system may also capture work, school and other common locations of the user.

Users who then use the calendar to track and create food and activity plans will build a large additional store of information for which advanced recommendation methods can also be employed as described below in more detail. A number of actions will be relevant including recording or confirming an actual behavior (tracked ate food or performed activity) which provides reasonable evidence that the user will likely try that item again (akin to "purchasing" an item). The action of placing an item in one's plan (akin to placing item in a "wishlist") and then not following through with the meal or activity, at the expense of a healthy and enjoyable item that might have been utilized, is an indicator of an item in which there is interested, but potentially advanced aid needed for follow-through. With any food or activity item encountered, be it through the calendar or by browsing options (akin to "shopping"), the user will be able to rate the item positively or negatively, just as with iTunes or Amazon.com books. This rating information can be used, along with their stated preferences from initial registration and questionnaires, in collaborative filtering, clustering and search methods employed to create personalized recommendations of foods and activities that users are not only likely to enjoy and keep in their Calendar, but also which users are likely to follow through on.

The recommendation and sharing unit 52 may include a preference based recommendations engine 52a (for new foods and/or activities), a healthy, goal based recommendation engine 52b for health and goals based recommendations, an unhealthy recommendation engine 52c for favorites and highly rated items recommendations and a unhealthy recommendation engine 52d for a user with no preferences and dislikes poorly rated items. To select one or more recommendations (a list of recommendations) for a particular user, the system uses filtering 50o that may include one or more of goal-based filtering, item-to-item collaborative filtering, user-based collaborative filtering, cluster modeling and search methods. Each type of filtering process produces one or more items which may be interesting to the user, based on their eating and activity habits and preferences.

The filtering rules used by the system will include heath risk and goal-driven rules that divide the initial recommendations table into healthy and unhealthy classes, based on the health risks and personal goals of a given user. Initially, the system will focus on normal weight/general prevention, obesity, overweight and underweight as the possible risks/conditions for a user—the most relevant concerns for the initial pilot population of college-aged youth—which are each linked to a baseline set of goals. These interventional goals drive recommendation settings related to calorie loss or gain settings, energy density selections for foods and basic healthy eating and activity habits that apply to all people. The system may also have more specific goals and recommendation rules for the following risks and conditions: history of cancer, early stage cancer, history of diabetes type 2, insulin resistance, diabetes type 1, diabetes type 2 with or without insulin, risk for heart disease, active heart disease, high cholesterol and high blood pressure. The personal goals of each user may be established by the individual through their use of the GoalGetter engine. The healthfulness of goals themselves will be assessed (i.e. user that sets goal of 20 pounds in 2 weeks will be given guidelines for more conservative weight loss based on their current weight), and personal goals will be merged with health-related goals, with overlapping goals only shown once.

In the system, after initial preferences are calculated and goals are used to filter preference-based recommendations and redirect unhealthy favorites to a substitution engine 50$p$ of the nutritional planning unit 50, then filters will be used to create enabling reports as shown in FIG. 2.

Based on User tables that track foods or exercises and amounts of foods eaten or exercise, frequencies and favorites/least favorites (like and dislikes) are used to determine frequency of items inserted in user's baseline and adaptive meal and exercise plans. User profile characteristics are also matched with other users using collaborative filtering, so items in matched users favorites are more frequently displayed in user's plan. Calorie requirements are calculated using recommended Institute of Medicine guidelines based on doubly labeled water studies. However, baseline plans constructed by our company, and many caloric and nutrient levels, are used as building blocks that can be pieced together or substituted to construct user meals and plans that meet their caloric and nutrient needs. These can be altered in real time based on user exercise calories burned and changes in preference, mood or location. Regarding location, a user can replace a recommended food on the fly with a food or meal at a nearby restaurant, as determined by our geolocation tools (both internal database and external APIs) and food tables inclusive of restaurant menus, in which the caloric and nutritional information of the prospective restaurant foods match the caloric and nutritional information of the item being substituted out.

Mapping is performed with our algorithms using the Topographically Integrated Geographic Encoding and Referencing system (TIGER) or other available geolocation web services to assess which will be used to generate mileage information and directions between user location and venue location. This information will be visualized in a table and users will be able to see their choices posted on a map. Directions will be displayed when clicking on the venue information for a particular recommended item within the calendar. Transportation preferences will further modify the location filter by calculating venue proximities from accessible public transportation stops, if preferred by the user.

Users can enter their other activities in their journal and calendar to visualize their complete schedule; this information can be used to exclude recommendations available at incompatible times (i.e. yoga class at same time as work) from being shown in their table of recommendations or shown in their calendar. Cost can be filtered based on the maximum amount users declare they are willing to spend on a particular class of items, such as groceries, eating out, outdoor activities, gym membership and other items defined in the succinct budgeting wizard. User declared requirements for handicapped access, such as ramps and facilities, can also filter out incompatible venues, or place a question mark next to those without data on the subject.

Each of these conditions link to a set of goals constructed based on clinical literature, internal expertise and consultants. For example, the daily recommended calorie level of an obese individual is be reduced such that the user loses 1 or 2 lbs per day. Or, if a doctor or dietitian prescribed a low calorie (1500 calories) diet, this will be incorporated into the individuals health filter, and an important part in selecting food items based on caloric density. If that person were also at risk for heart disease, the at risk for heart disease maximum cholesterol threshold would filter out foods generated by recommendation algorithms, and would place high cholesterol foods designated as favorites by the patient in a Healthy Substitution Recommendation Wizard.

Returning to FIG. 2, the nutritional planning unit 50 may further comprise a favorite and/or least favorite food module 50$a$, a favorite and/or least favorite activity module 50$b$, a food history module 50$c$ and an activity history module 50$d$ that capture the above user information using, for example, a food and activity form that is filled in by the user. The nutritional planning unit 50 may further comprise a food rating and activity rating modules 50$e$, 50$f$ that capture the user's ratings using, for example, a click and rate form. The nutritional planning unit 50 may further comprise a personal goals module 50$g$ that captures the health and/or fitness goals of the user using, for example, a goalgetting module 50$q$ that gathers data from various sources as shown in FIG. 2. The nutritional planning unit 50 may further comprise health risks module 50$h$ that captures the health risks of the particular user using, foe example, health forms. The nutritional planning unit 50 may further comprise a special needs module 50$i$, a locations module 50$j$, a transportation needs module 50$k$, a schedule module 50$l$, a budget module 50$m$ and a demographic module 50$n$ that captures various pieces of data, such as by using registration and user profile data.

Figure 3:
FIG. 3 illustrates an example of a user interface of a FitNet website that is part of the community-specific and personalized nutrition and activity planning system.
Figure 4:
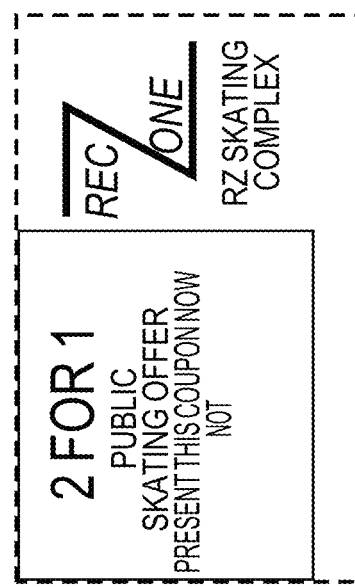
FIG. 4 illustrates an example of a scorecard user interface of the FitNet website that is part of the community-specific and personalized nutrition and activity planning system.
Figure 5:
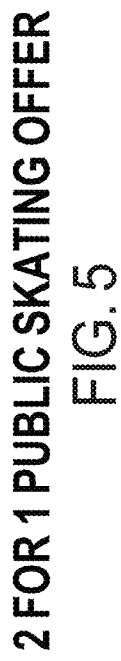
FIG. 5 illustrates an example of a coupon user interface of the FitNet website that is part of the community-specific and personalized nutrition and activity planning system.

A website and web-based software, known as FitNet GoalGetter, may be part of the community-specific and personalized nutrition and activity planning system. The GoalGetter module 50$q$ (whose user interface is shown in FIGS. 3-10) allows users to create their own personalized healthy lifestyle plan, confidentially track progress, and automatically receive electronic rewards for achieving goals related to the plan. The tools can also be used to design a plan for and deliver rewards to one's child, spouse, students or employees. For example, the GoalGetter system may be used to set up the core 5 point Drive 2 Fitness program (1 point each for: an hour or more of physical activity, an hour or less of TV or video game time, no sugar added beverages, 8-11 hours of sleep and a bonus for doing all 4 in a day) and an administrative user of the system only has to enter the number of goals, the name of each goal, the performance threshold(s) for each goal and whether it is binary or categorical, how often these goals are tracked, and a graphic denoting each goal. The administrative user then can choose from basic graphical templates for different types of users, such as the one Fitness Forward chose for elementary-aged school children as shown in FIG. 3 which shows the goals, week view of points tracking calendar, and reward sponsors. FIG. 4 shows an example of a monthly view of the calendar of the GoalGetter module and FIG. 5 illustrates an example of a reward voucher of the goalgetter module.

The user/administrator can also enter additional links, graphics and interactive tools to provide education about each goal using a "what you see is what you get" content management system that allows direct editing of HTML pages, akin to editing a Microsoft Word or Powerpoint document. The tracking of points is achieved using one-click checkmarks (binary outcomes; see points tracking on FIG. 3), slider bars (categorical outcomes) or entry forms for real numbers, converted automatically to a categorical variable based on thresholds set by the administrator. For long-range goals such as weight status and effort, the administrator can also create additional questionnaire-completion, usage and performance bonuses with required completion intervals and for which their customers can earn additional points towards rewards.

In the system, most rewards are managed electronically. An image of a rewards voucher with an ID number is generated for the individual to print as shown in FIG. 5. Rewards sponsors can login to the system to keep track of people who have printed off their voucher or used a voucher code online (for electronic music or online stores) to claim their reward. Electronic rewards drastically improve the cost-effectiveness of programs and have been correlated with increased end-user participation in the online portion of the program. The GoalGetter module is also available to administrative users, such as researchers or worksite health managers, who want to build short and long-term goal programs for their own customers. The system also may have ready-to-use programs for activity and nutrition for college-aged youth, adults, patients suffering particular ailments and physicians.

Figure 6:
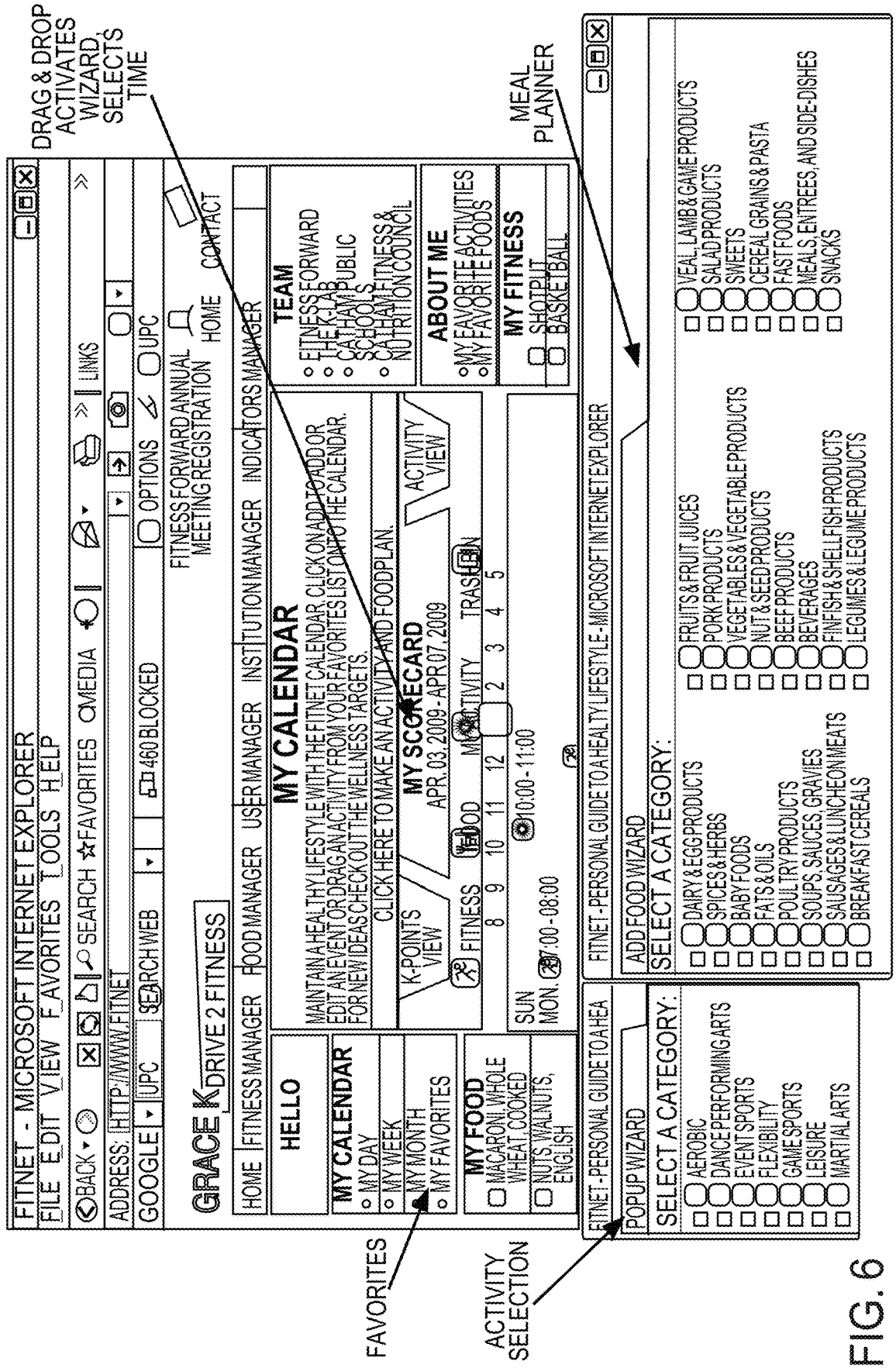
FIG. 6 illustrates an example of another user interface of the FitNet website that is part of the community-specific and personalized nutrition and activity planning system.

In order to enable advanced behavior tracking that quantifies actual activities and nutrition, the module has an interactive calendar that allows users to drag-and-drop Food and Activity icons onto their personal calendar, or enter them into an online scheduler akin to desktop calendar programs and advanced journal programs (as shown in the example user interface in FIG. 6). The interactive calendar captures a wealth of information about user preferences and habits. For example, food and activity (physical activity, sleep, etc.) journaling is typically a short-term intensive activity, and the accuracy of self-reporting can be questionable so that the system assesses when users are actively tracking information and when they are not in order to determine data reliability over various periods of time. The system also encourages frequent but brief duration use using bonus points and rewards, and can be interacted with using computing devices to increase frequency and accuracy of reporting.

The system provides the ability to upload quantitative assessments of physical activity (such as pedometers) and nutrition (pre-packaged meals UPC code scanner) to the system. In addition to tracking, the system can also be used to create a personal Food and Fitness plan as far into the future as the user wishes. Planned versus actual behavior can be calculated in order to help users make realistic refinements to their daily objectives. The food and fitness tracking calendar is built on the FitNet Food and Activity databases. The FitNet Food database is a reorganized and annotated version of the *USDA National Nutrient Database for Standard Reference, Release* 17-23. See U.S. Department of Agriculture, Agricultural Research Service. 2004. USDA National Nutrient Database for Standard Reference, Release 17-23. Nutrient Data Laboratory Home Page, http://www.nal.usda.gov/fnic/foodcomp. Food descriptions are split into additional codified categories, plus additional attributes for food items have been created including allergy flag, health restriction, health promotion, preference restriction (i.e. vegan, kosher, etc.), cultural relevance, ingredients of, ingredient for and meal inclusion, among others.

The system's activity database 54b creates a hierarchy for activities that is built for usability and ease of comprehension by the end user. Data linked to each type of activity include activity type, activity subtype, specific activity, rate of caloric expenditure based related to intensity and duration, required equipments and environments for performing the activity and ancillary gear used for activity, among other information. The rate of caloric expenditure also links to classifications of activities related to their primary physical benefits, such as aerobic/cardiovascular, strength, speed, flexibility, etc. In order to create, manage and continually update these databases, we have constructed the FitNet Manager, which allows a non-technical user to easily view, add and modify the database (See the user interface examples in FIGS. 7 and 8).

Finally, to enable community-specific nutrition and activity recommendations, the system has developed a Food and Activity Venue Directory for the United States. In one example shown in FIGS. 9-10, a Food and Activity Venue Directory with detailed annotations for the Raleigh-Durham-Chapel Hill, North Carolina ("NC") venues, including Duke University sites may be part of the system. Both Food and Activity Venues contain general information about the venue, such as name, location (city, state, zip, longitude, latitude), contact information, hours of operation at different times of the year, customer restrictions such as age or gender (common for many gyms), general category of business as denoted by the North American Industry Classification System (NAICS) and Standard Industry Classification (SIC) codes, plus advanced menu, inventory, activity and equipment information. Detailed annotations of the directories with menu, inventory, activity and equipment information depend directly on the structure of the Food and Activity Reference databases. For example, restaurants, convenience stores and supermarkets are all loaded into the Food Venue Directory, using the FitNet Manager. For a typical NC restaurant such as McDonald's or Bullock's BBQ, each food item on the menu is listed, including information on price and annotated nutrition information based on FitNet's Food Reference Database (which includes food information from commercial vendors). In many cases, smaller restaurants do not have nutrition information available; one aim of FitNet is to create a platform which allows users to easily search across nutrition information of various restaurants, thus making it a competitive advantage for a restaurant to publish this information. For retail food stores, inventories of food items are entered with similar types of information, all typically linked to the UPC or SKU code for each item. An organization's Menu can be uploaded in batch from a spreadsheet or text file using a standard FitNet format; items can also be entered individually as menus change. While FitNet staff create the initial annotated directory, our aim is to ultimately link with the internal systems of large chains or allow restaurant manages to enter information on new items or venue information such as hours in order to automate updating of our databases. As our population of users grows, venues will be willing to do this to stay competitive with other venues any healthy offerings, drawing customers amongst FitNet users.

In the system, annotated information for Activity Venues varies more with venue compared to Food Venues. FitNet Manager allows FitNet staff or the manager of an Activity Venue to log simply the equipment or environments available at the venue (i.e. "treadmill," or "lake") FitNet's Activity Reference Database automatically populates the Venue Activities with all activities that can be performed with a given equipment or environment, allowing spot correction or additions afterwards, where necessary. Allowing the FitNet Manager user to enter tangible equipment terminology is typically much easier than having to match activity terminology from various venues to the exact terminology used by FitNet, even with synonyms linked in our databases. FitNet Manager also allows the insertion of Membership types and costs, Class schedules and Sports team schedules common at gyms and universities. In addition to FitNet staff, these tools are also being tested with venue managers, including park managers and gym managers, so that the tools can be optimized to facilitate real-time information updating directly from venues.

Leveraging the extensive work already completed on GoalGetter goal, tracking and rewards software, and the interactive food and activity tracking calendar and the FitNet Food and Activity Reference Databases and Directories, FitNet is now poised to construct a robust recommendation engine to generate a personalized food and activity plan directly into the users calendar, using community-specific information from FitNet databases, and then facilitating goal setting and rewards for following this healthy lifestyle plan.

Figure 12:
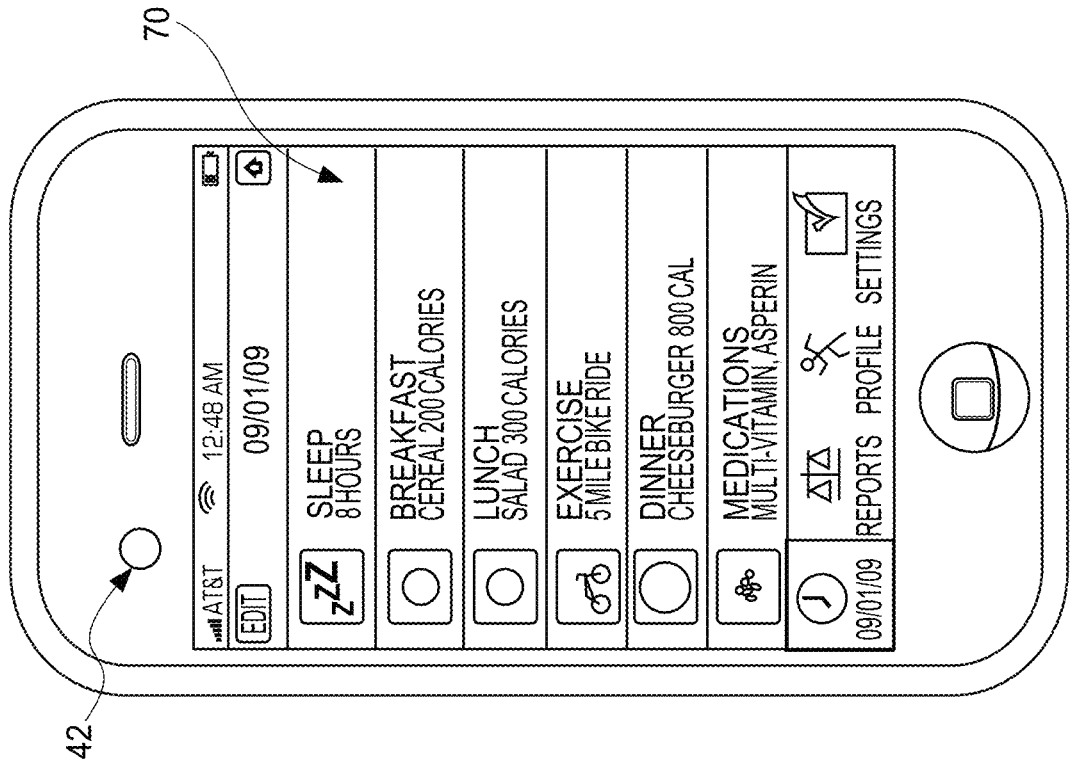
FIG. 12 illustrates an example of a computing device with a computing device app that can interact with the community-specific and personalized nutrition and activity planning system.
Figure 11:
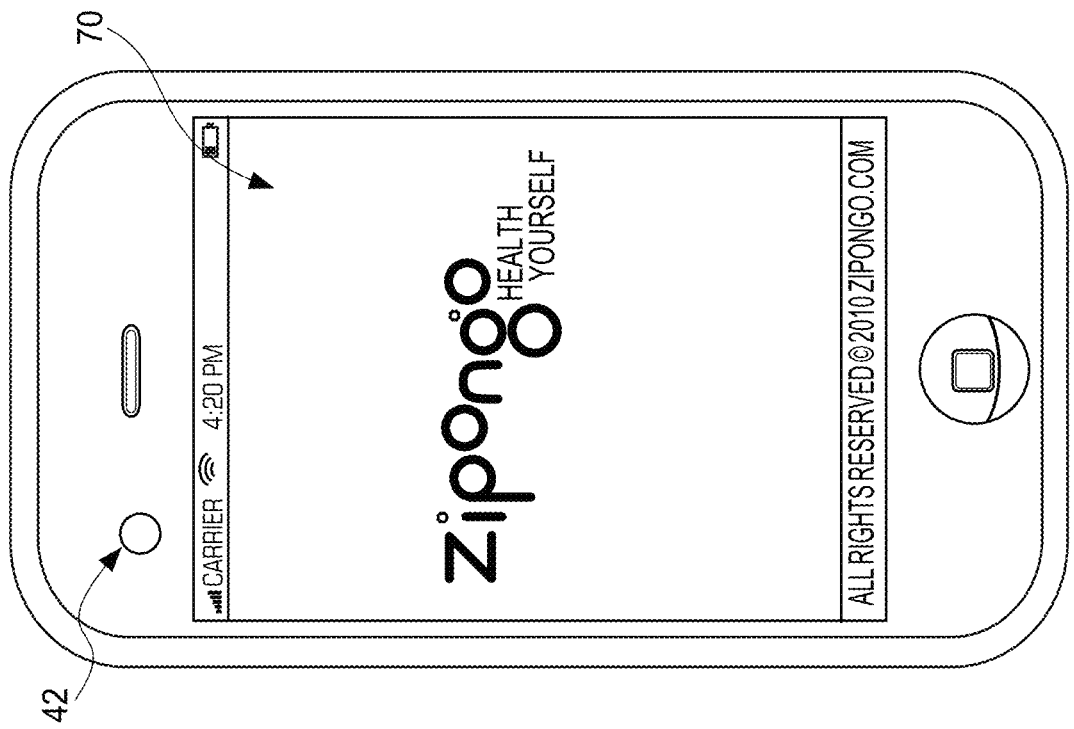
FIG. 11 illustrates an example of a splash screen of the computing device app.

FIGS. 11 and 12 illustrate an example of a computing device 42 with a computing device app 70 that can interact with the community-specific and personalized nutrition and activity planning system. In particular, the computing device 42, such as an Apple iPhone in this example, stores an app in memory of the computing device 42 and the app contains a plurality of lines of computer code that are executed by a processing unit of the computing device 42 to implement the functions and operations of the computing device app 70. The user interface of the computing device app 70 may have a journal tab, a reports tab, a profile tab, a friends tab, a gobody (game) tab, and a more tab.

Figure 13:
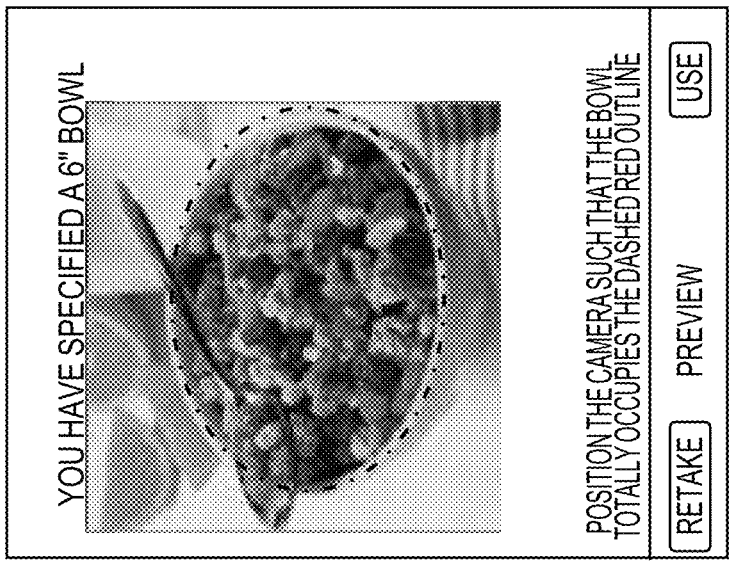
FIG. 13 illustrates an example of computing device app user interface for determining an amount of a portion of a meal using the community-specific and personalized nutrition and activity planning system.

FIG. 13 illustrates an example of computing device app user interface for determining an amount of a portion of a meal using the community-specific and personalized nutrition and activity planning system. In particular, the user captures an image of the food item being consumed (such as the bowl of cereal shown in FIG. 13) and the system is able to approximate the caloric information about the food item so that the user does not have to try and estimate the caloric information about the food item. This is achieved by asking the user to report the size of the dish the food is contained by, or the portion of food itself, using an on screen ruler. With that information entered, the application can then provide a shape, such as a circle, within which the user can fit the plate or portion of food they are trying to estimate. This allows the system to calculate the distance from which the camera device was from the food and dish objects. Surface area can then be estimated based on the reference value on either the plate or food portion(s). Identification of the food, either by the user or by our combined visual recognition, location subsetting and voice word suggestion subsetting, can then provide the density of the food and standard portion sizes (the prior information), and allow estimation of the weight, and thus also nutrient information, for that portion of food. Flash to image capture time, and metadata such as time of day, level of lighting, and camera device used can be used to calibrate both visual recognition for identification and portion size estimate purposes. User voice and text comment recordings can also be incorporate to refine portion size estimations.

Figure 15:
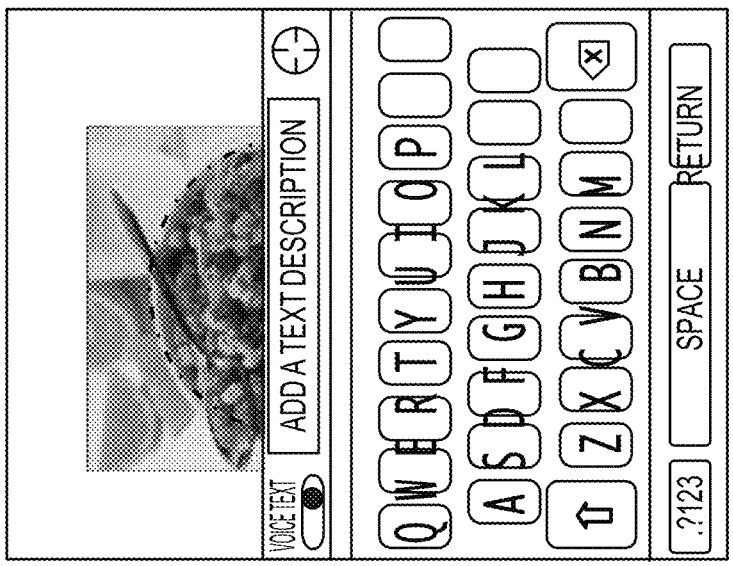
FIGS. 14 and 15 illustrate an example of computing device app user interface for adding a voice annotation and a text annotation, respectively, to a meal image.
Figure 14:
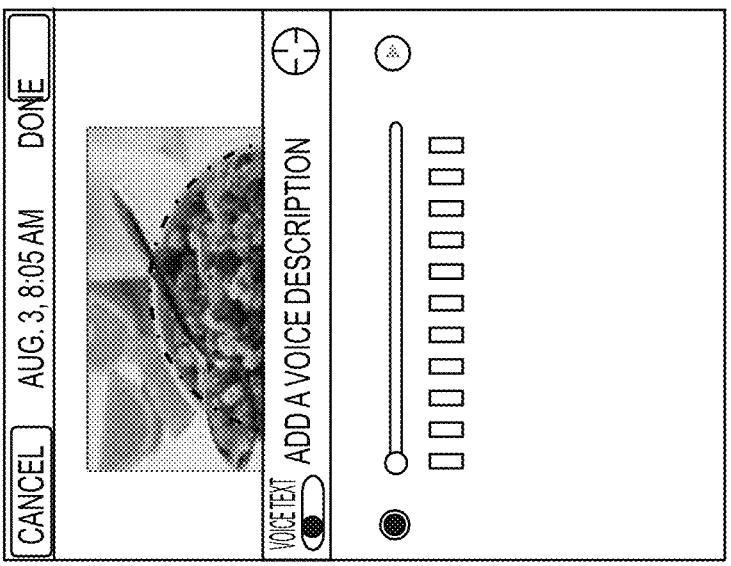

FIGS. 14 and 15 illustrate an example of computing device app user interface for adding a voice annotation and a text annotation, respectively, to a meal image. Once a user has captured an image of a food item, the computing device app allows the user to add a voice annotation (FIG. 14) or a text annotation (FIG. 15) for the food item that is then stored along with the other food item information for the particular food item.

Figure 16:
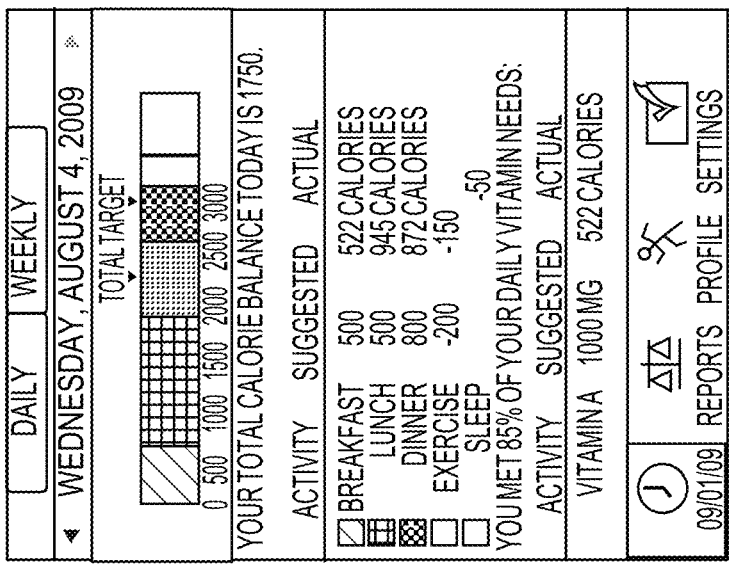
FIGS. 16 and 17 illustrate an example of computing device app user interface for selecting and tracking a breakfast meal using the computing device app.
Figure 17:
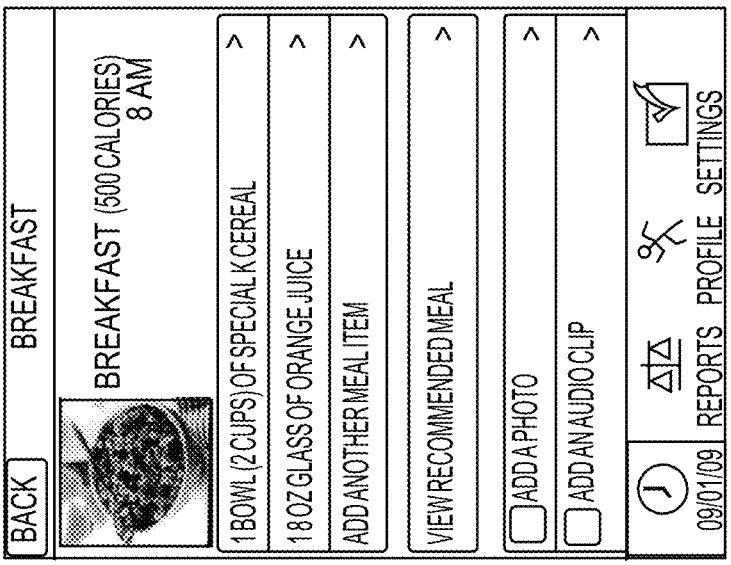
Figure 18:
FIG. 18 illustrates an example of computing device app user interface for daily or weekly caloric intake tracking using the computing device app.

FIGS. 16 and 17 illustrate an example of computing device app user interface for selecting and tracking a breakfast meal using the computing device app and FIG. 18 illustrates an example of computing device app user interface for daily or weekly caloric intake tracking using the computing device app. As shown in FIG. 16, once the user images the food item, the system perform an automatic analysis of the food item and the resulting analyzed meal is shown in the user interface in FIG. 17. FIG. 18 illustrates the daily and weekly caloric intake of the particular user.

FIGS. 19A and 19B illustrate an example of a journal user interface 80 of the computing device app and FIG. 19C illustrates an example of a guide user interface 86 of the computing device app. In the example in FIG. 19A, the user interface may include an add entry portion 80a for adding a new meal, food or activity into the daily plan for the user, a progress portion 80b that shows the progress of the user against the calorie counter of the system and an options portion 80c that shows recommendations/options for the user to select as part of their plan. The user interface also may have a date picker that adds List View like iCalendar (Week view) or a month View using colors to show when over or under calories or apply other reporting filters. The user interface may also have a portion that shows meals and activities (samples) for the user and list the needs remaining for today, such as for example, 958 more Cals in, 2 svg fruit, 3 svg veggie, 2 svg grain, 1 svg meat/bean, 2 waters 500 Cals out of exercise calories and 8 hours of sleep. The user interface also may include a My Day-Tracked Items portion. FIG. 19B shows another example of the journal user interface that shows the entries, the total calories eaten and the total calories remaining for the time period (a day is this example). The journal user interface 80 is unique in allowing users to add pictures, new foods and new nutrition info (or exercises) with data associated with pictures—enabling improved database and improved visual recognition, as well as picture sharing.

The guide as shown in FIG. 19C (such as the sample plan for a day shown in FIG. 19C) that is personalized to the user can be generated based on various data. In particular, the personalized plan is generated from journal and device data, plus Profile data (height, weight, age, sex, weight goal, daily physical activity goals, other health, food and fitness goals, food and physical activity preferences (self report, thumbs up and down in Zipongo journal, Facebook integrated data), locations & convenience factors, schedule, budget and price sensitivities, relationship to what friends are doing and their schedule).

Figure 20:
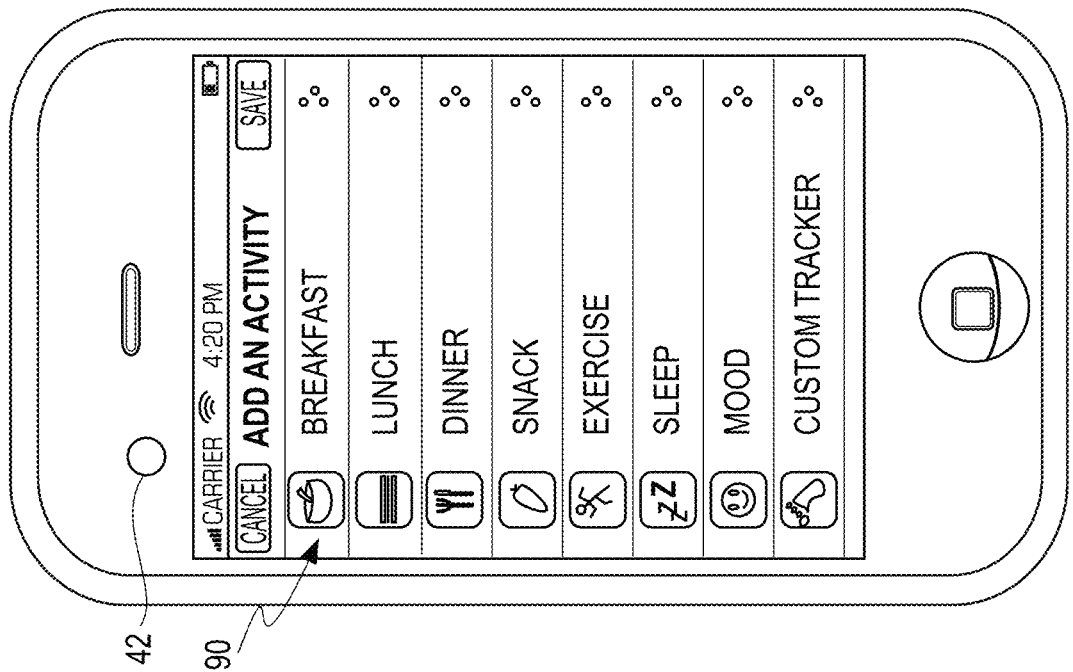
FIG. 20 illustrates an example of an add an activity user interface of the computing device app.

FIG. 20 illustrates an example of an add an activity user interface 90 of the computing device app. The add an activity user interface 90 allows the user to add meal food items, exercise items, sleep entries, mood entries and custom items into the user interface. All of the information entered into the computing device app is communicated back to the community-specific and personalized nutrition and activity planning unit 46 over a link so that the data can be used to determine goals, etc. by the system for the particular user. The computing device app timestamps when each item is added. For the breakfast, lunch and dinner entries, the computing device app permits those entries to be added once per day. If a user has already added a breakfast, for example, the app will take the user to the meal, such as the breakfast, that the user already started. When the user has multiple adds per day for entries other than breakfast, lunch and dinner, the computing device app may do the following: 1) for snacks, when selected, the entry is changed to Snack/Water/Drink Break; 2) for exercise, when selected, if an Exercise/Workout/Physical Activity has already been added that day, user gets option on next screen to use add new Activity to already started Exercise/Workout (this is important for the gym, weight lifting, body circuits/circuit training/Curves, etc). Within Exercise, they can add activities; 3) for sleep, if a Sleep session has already been added (like a Nap), user can add to that session or start a new session (within a sleep session, user can either note going to sleep, waking up, or note times when your sleep was disturbed; and 4) for the customer Tracker, events (i.e. Headache), if the event is already on the tracker list, and user already tracked an earlier headache in Day, gives option to add annotations to previously added headache, or add new one. The mood entries may permits multiple adds and, each time user clicks, they just rate current status with Smiley Face Schema.

Figure 21:
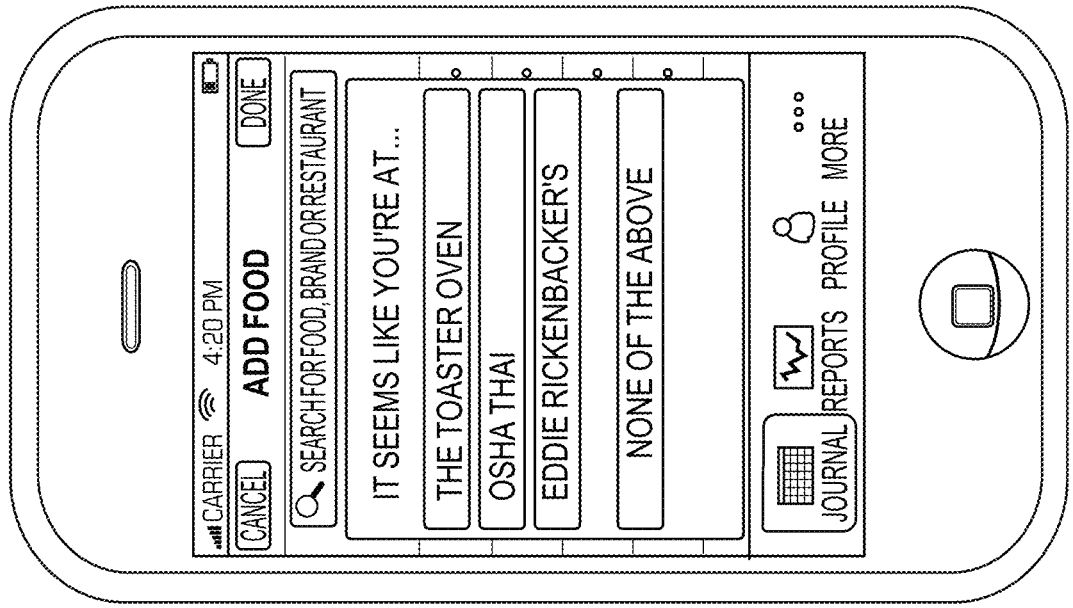
FIGS. 21-23 illustrate examples of an add a food user interface of the computing device app.
Figure 23:
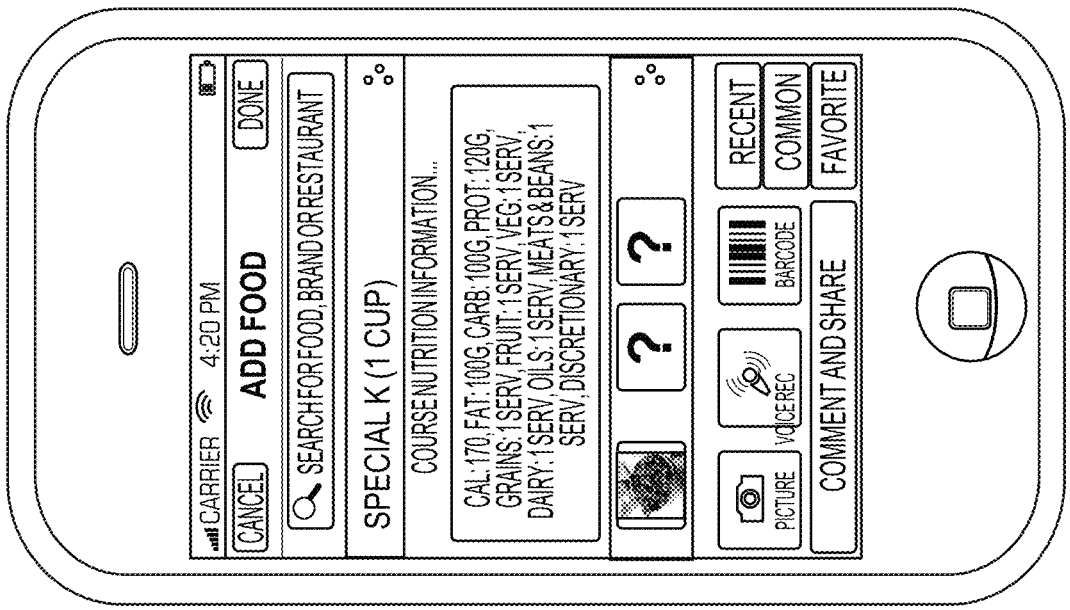
Figure 22:
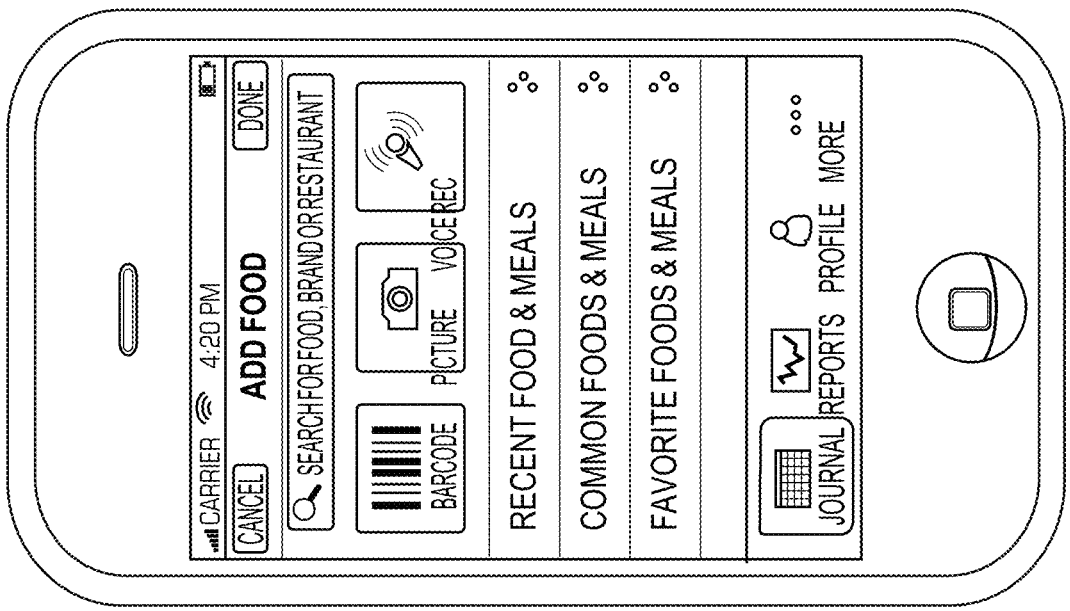

FIGS. 21-23 illustrate examples of an add a food user interface of the computing device app. In FIG. 21, the computing device app, when operating on a computing device with location determining capabilities, provides the user with a list of possible locations (restaurants or the like) in which the user is located when the user wants to add a food entry. FIG. 22 shows an example of a search for food, brand or restaurant window that also allows the user to browse recent foods/meals, common foods/means and/or favorite food/meals to add a new food entry into the computing device app. Common foods are defined and weight in a two-fold manner. The first is curated flags on foods that are deemed to be more common by experts. The second are foods that are searched and tracked most frequently, both on our system, and other open search system that provide freely usable analytics on search frequency. FIG. 23 illustrates the user interface portion that shows details of a particular food selected by a user.

Figure 24:
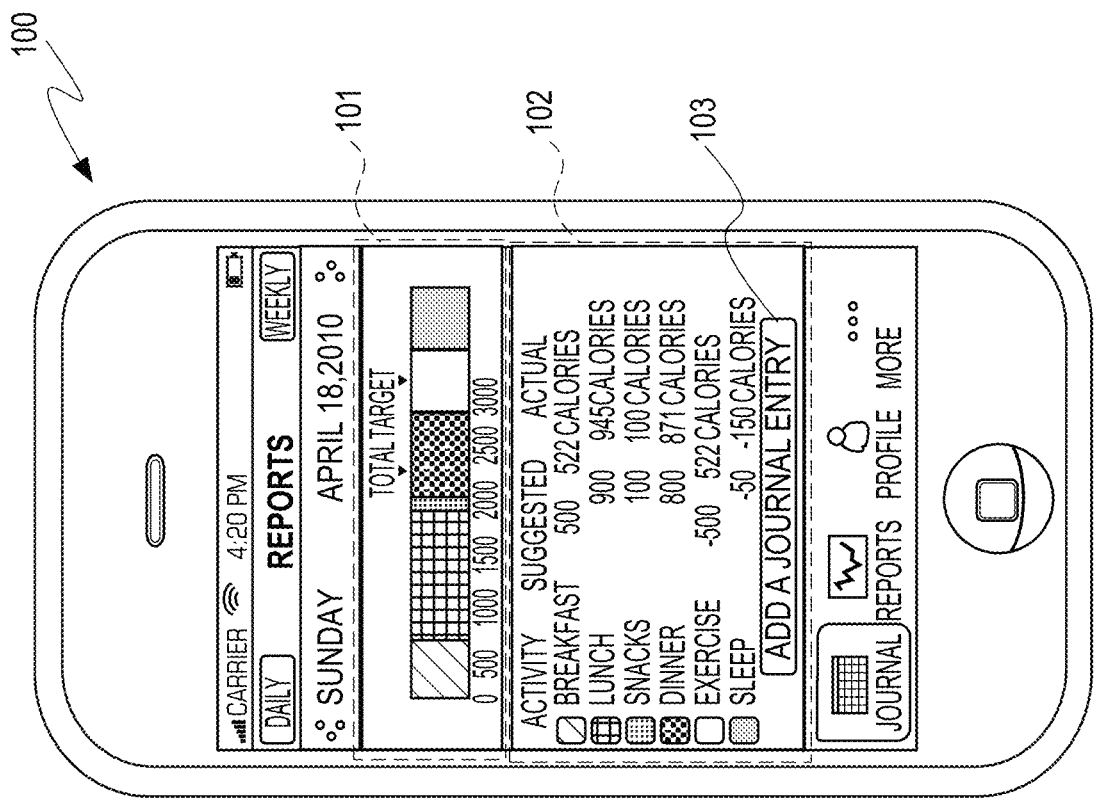
FIG. 24 illustrates an example of a reports user interface of the computing device app.

FIG. 24 illustrates an example of a reports user interface 100 of the computing device app. The report may show various information on a weekly or daily basis (the daily one is shown in FIG. 24). For the daily report, it contains a summary portion 101 that graphically shows the user's current caloric intake against the target amount (with the different entries being coded), a entry detail portion 102 that shows each entry, the suggested caloric number for the entry and the actual caloric number for each entry and an add a journal entry portion 103 that allows the user to add a new entry.

Figure 25:
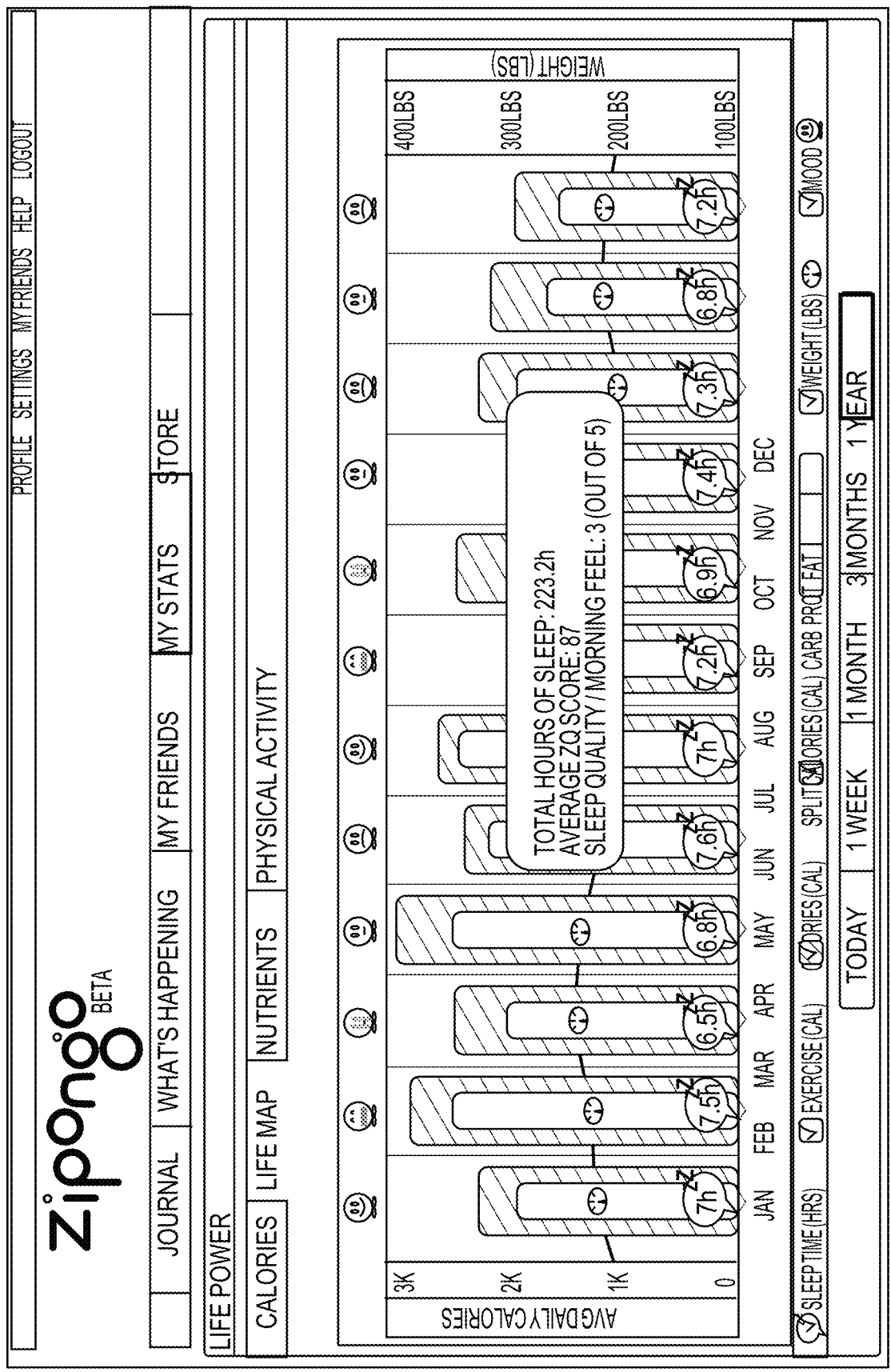
FIG. 25 illustrates an example of a life map user interface that can be displayed on a computing device.

FIG. 25 illustrates an example of a life map user interface of the computing device. The life map has a variable time period (1 day, 1 week, 1 month and one year, for example) and shows each entry with a particular pattern or color so that each entry is viewable on the life map. The life map is a graph of various items (calories, protein or fat, for example) over the period of time that was selected by the user. In the system, the data from the various computing devices as described above and a user's self-report online and mobile journal can be aggregated into the "LifeMap" shown in FIG. 25. The lifemap may contain data about various categories (calories, exercise, weight and mood and graph those pieces of data over a timeframe as shown so that, among other things, the user can see the trends over time.

Figures 26, 27:
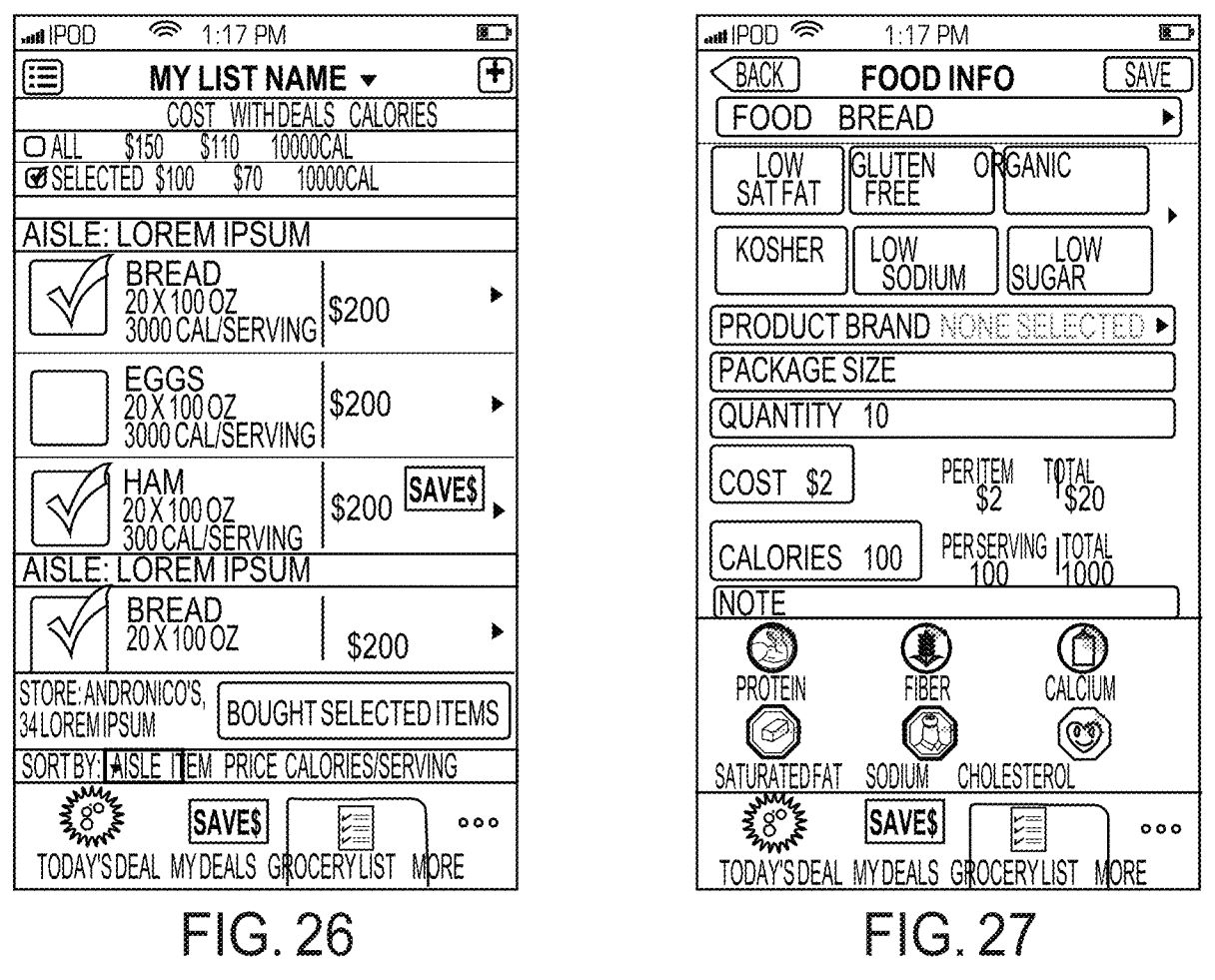

FIG. 26 illustrates an example of an automatically generated grocery list of the computing device app. The automatically generated grocery list allows the user to have their grocery list generated based on the recommendations made by the system. In addition, as shown in FIG. 26, items in the grocery list (like the ham in the example) are linked to deals as well as store inventory so that the grocery list may be separated up by the store in which the particular food item can be purchased by the user. FIG. 27 illustrates an example of food information user interface of the computing device app in which the details of the food item (cost, calories, fat, fiber, etc.) are graphically displayed to the user.

Figure 28:
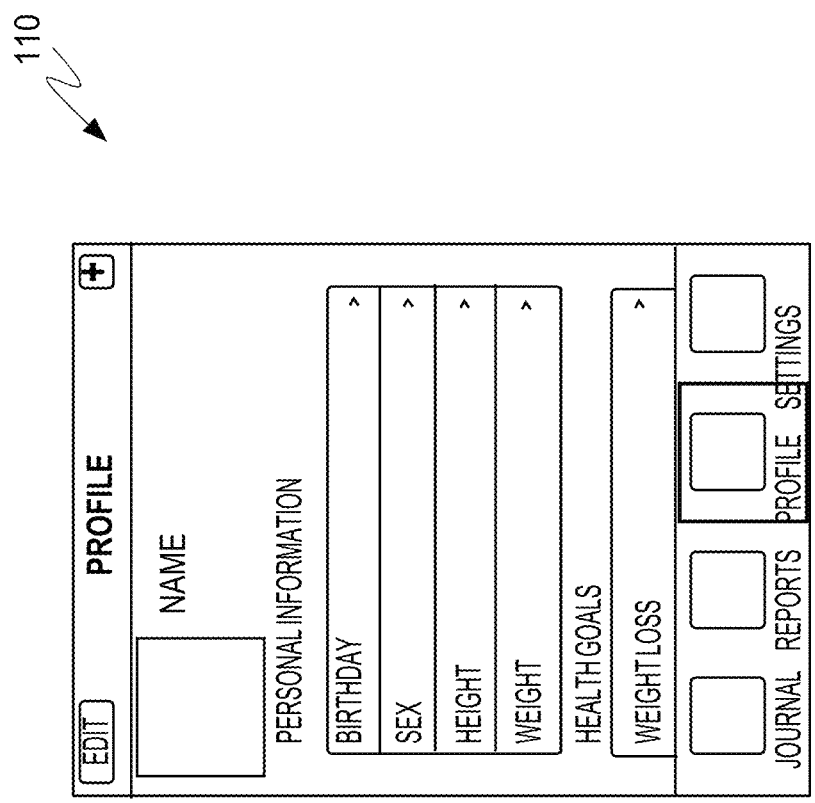
FIG. 28 illustrates an example of a user profile user interface of the computing device app.

FIG. 28 illustrates an example of a user profile user interface 110 of the computing device app. The profile user interface may have a minimal profile screen to get the basics at registration or may be the same initial profile user interface and then additional screens that allow the user to provide additional profile information. The user profile user interface may be an editable form in which the user can supply one or more pieces of information such as name (comes from registration), email address, self photo, the year/month/date of birth (age), sex, height, weight, and current activity level (same categories as used for recommendations). The user profile user interface also may include health goals of the user such as a weight loss target (the app may show target weight range for height (based on BMI ranges) and the user enters goal weight or pounds want to lose (lbs or kg), and by when (date), an activity level target—how active do you want to be? (Same categories as above), and custom goal targets such as the name of goal/target, + or –, Value, Measure, Date by when.

FIGS. 29A-C illustrate examples of a breakfast, lunch and dinner user interface, respectively, of the computing device app.

FIGS. 30A-C illustrate examples of a barcode/UPC scanning process using the computing device app. In this example, the user can scan a barcode/UPC label in order to identify the food item. Thus, the user adds a picture/image/upc code/voice data to the milky way, add another food with Milky Way via search bar, or start by adding a new food course in green box below (w/search, UPC/pic/voice). In this scenario, the system uses the UPC code with new Food Course.

Figures 31A, 31B, 31C:
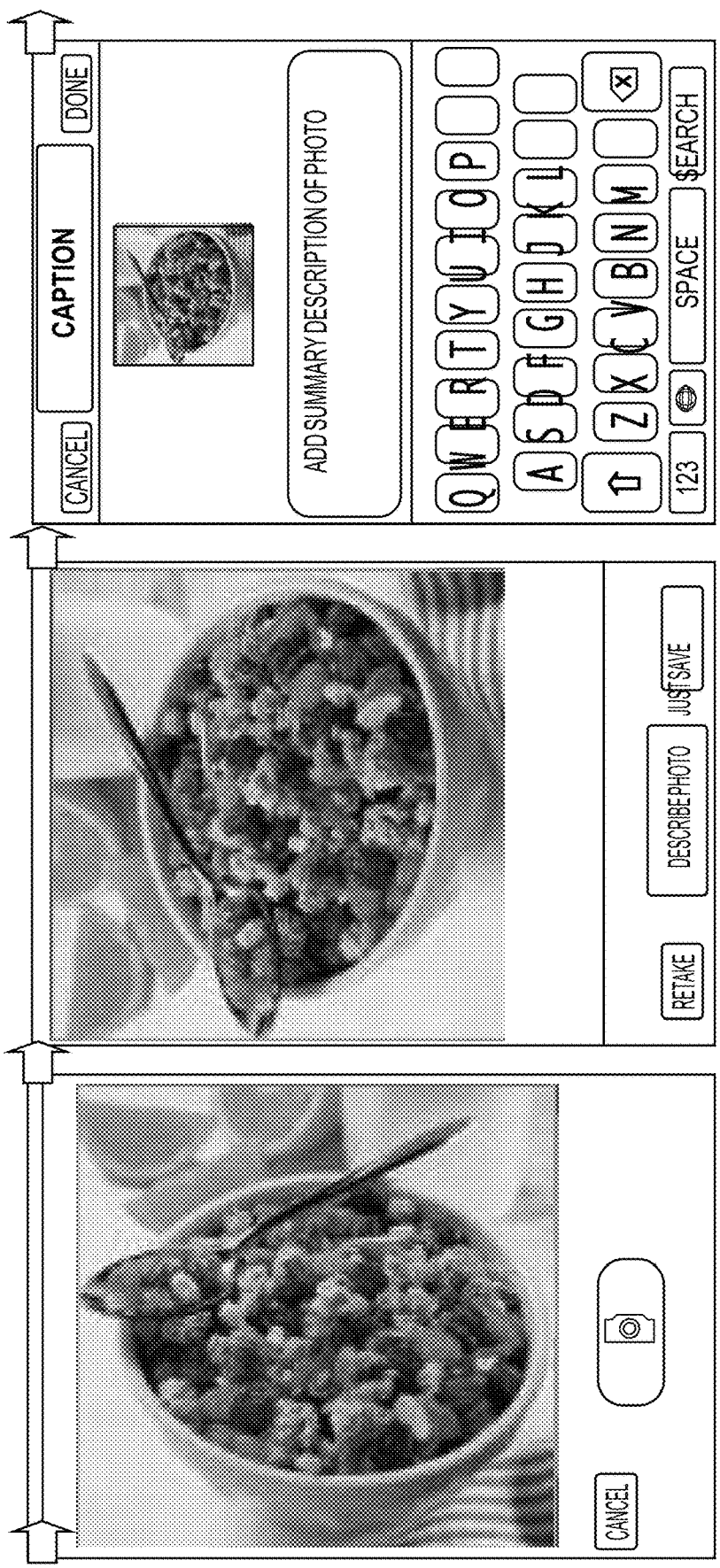
FIG. 31A-C illustrate examples of a meal capture image process using the computing device app.
Figure 34A:
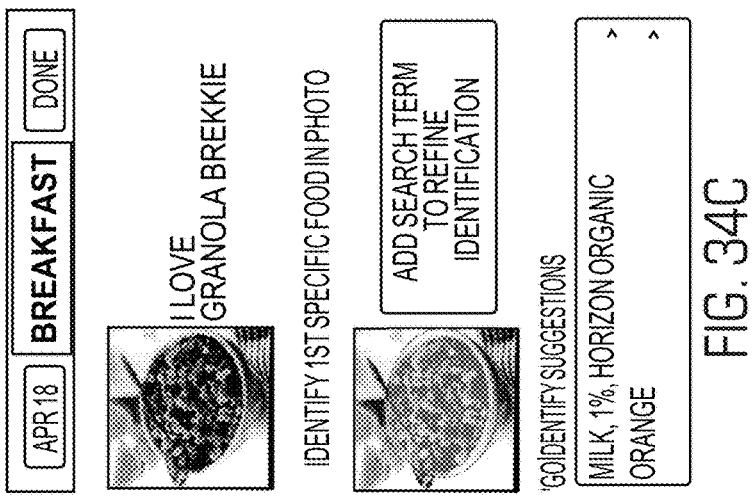
FIGS. 34A-D illustrate examples of a meal capture image process with suggestions using the computing device app.
Figure 34B:
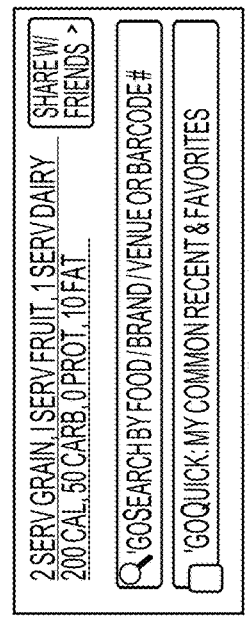
Figure 34C:
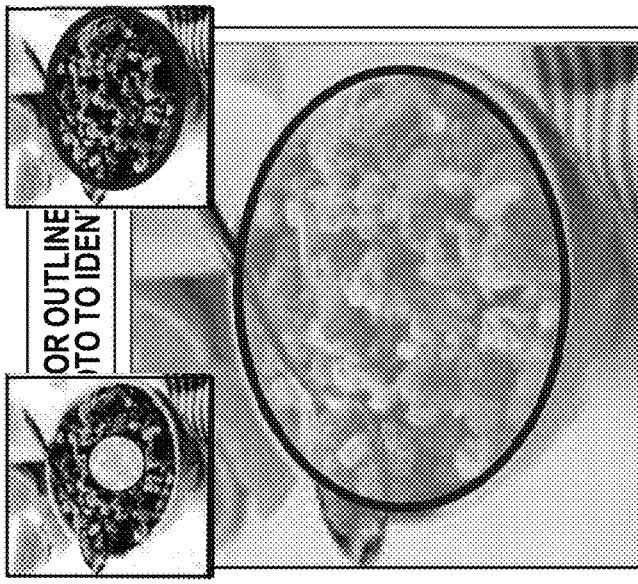
Figure 34D:
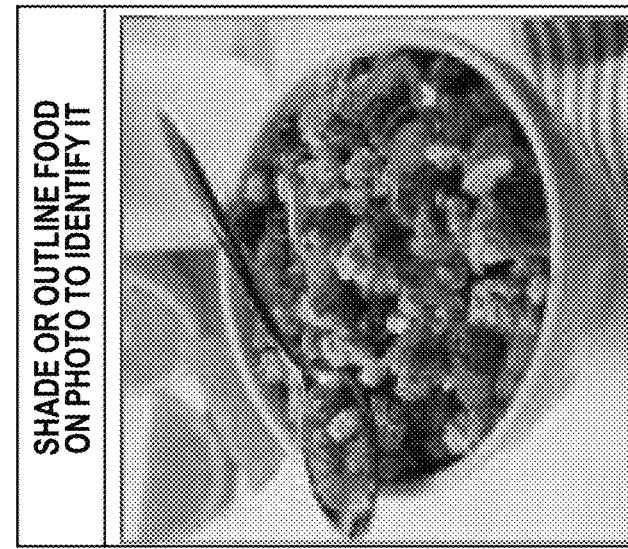

FIG. 31A-C illustrate examples of a meal capture image process using the computing device app. First, the user clicks on a photo icon and the user is shown the standard camera interface of the computing device in which the user can use a profile or a landscape view. After the photo is taken, the user can choose to use photo or retake and should be compressing the photo in the meantime, regardless, in anticipation that they will use the photo; this will speed up the process when they select "Use" (and can just scrap pic after hit reuse). The user interface may keep a full screen photo for viewing and tagging, and a thumbnail for annotating and calendar. If the user selects "Just Save", then the user is returned to the journal view. If the user clicks on "Describe Photo", the user has the opportunity to add photo with a caption for whole photo: Some users may put dominant or only food name (Granola cereal') or Brand Name "Kashi GoLean Crunch." Others may put a summary like: 'The Breakfast I made myself' or a funny comment/description like "Sweet granola."

FIGS. 32A-C illustrate examples of a meal capture image process with prior barcode scanning using the computing device app in which the user tags and identifies the photo with the UPC code being already scanned by the user. Since the UPC code was already scanned, the computing device app inserts the "Cascadian Farms Fruit & Nut Granola" into the user interface due to the UPC code scan. In this scenario, the user first shades or outlines the food on the phone that identifies the food as shown in FIG. 32A.

FIGS. 33A-C illustrate examples of a meal capture image process without prior barcode scanning using the computing device app in which the user tags and identifies the photo without the UPC code being already scanned by the user. In this scenario, the user first shades or outlines the food on the phone that identifies the food as shown in FIG. 33A. The 'goIdentify window (search based on prior text comments like 'granola', picture recognition, GPS-based menu finder, voice recognition, and common/recent/favorites (1% milk) eaten around that time. Already identified items (the cereal in this example) show up in blue, and are excluded from the 'goIdentify results. User can find other food brands by clicking on suggestions or adding search terms. FIGS. 34A-D illustrate examples of a meal capture image process with suggestions using the computing device app in which the app provides suggestions without tagging.

Figures 35A, 35B, 35C:
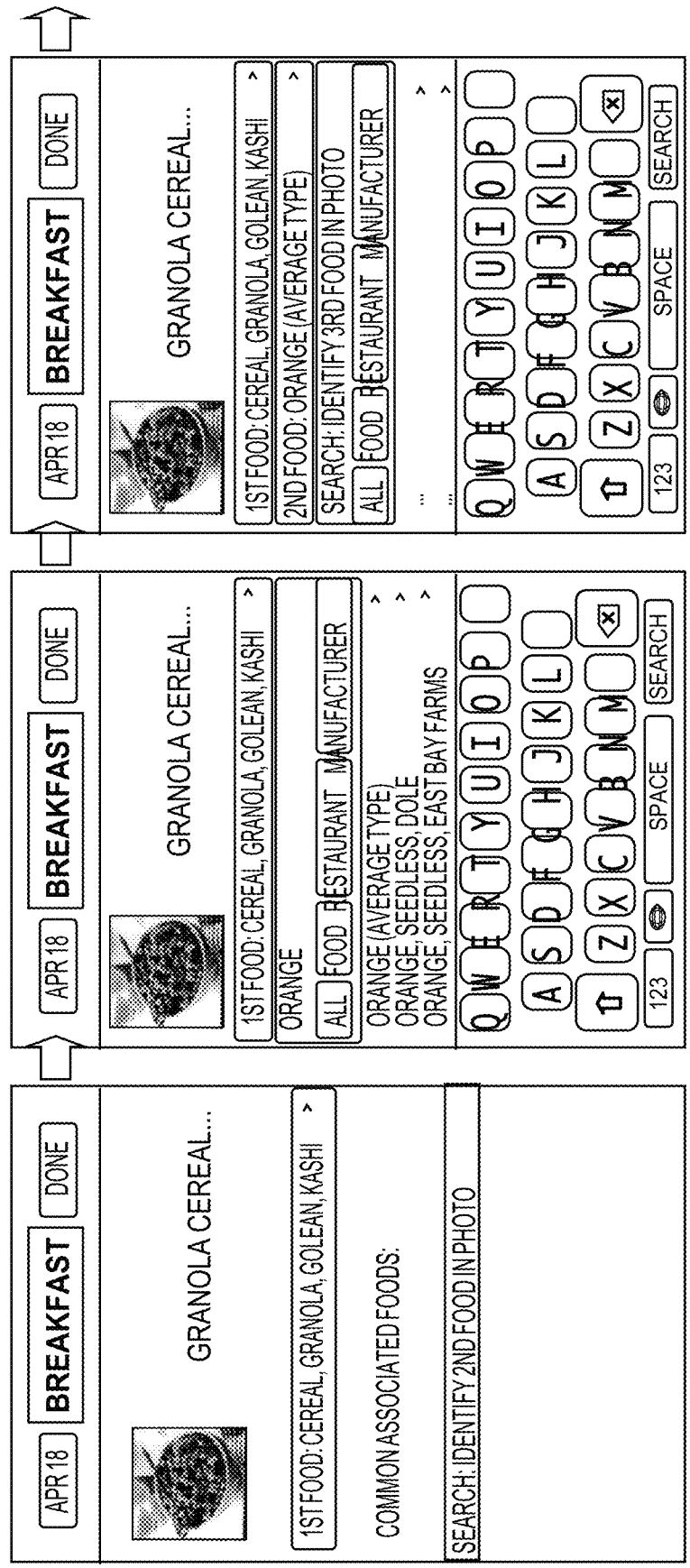
FIGS. 35A-C illustrate examples of a photo tagging process using the computing device app.
Figure 36B:
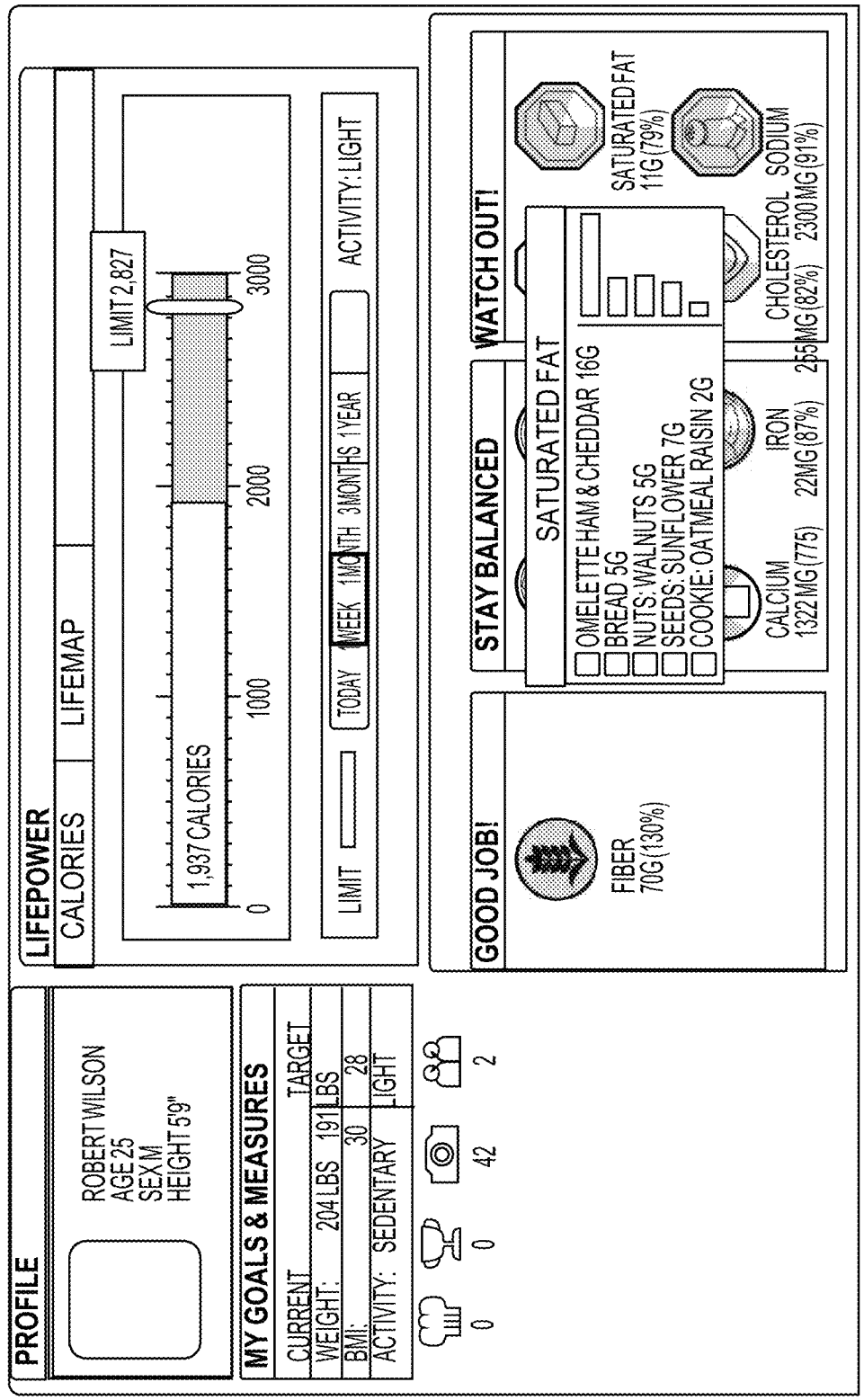

FIGS. 35A-C illustrate examples of a photo tagging process using the computing device app. Note: If UPC(s) already scanned, those specific foods already added. User is asked (FIG. 35A) to "Identify 1st specific food in photo," using the classification scheme from the database. The "1st" term is key, as it puts users in mindset of picking out separate foods. Since most users tag photos with descriptions of the dominant food, this will already by auto-populated in the search, but, highlighted, so user can either press next to the right of it and add more search terms, or just type over it if they had a random description about the meal. In the user interface in FIGS. 35B and 35C, the user "Identify 1st specific food in photo," using the classification scheme from the database. The "1st" term is key, as it puts users in mindset of picking out separate foods. Since most users tag photos with descriptions of the dominant food, this will already by auto-populated in the search, but, highlighted, so user can either press next to the right of it and add more search terms, or just type over it if they had a random description about the meal.

The system may also provide emailing or SMS/MMS food to friends. Optimally, as a user starts typing, names are suggested from address book on the computing device, just as when the user is writing an e-mail. The user can also select multiple friends and the app separates each email or mobile phone number with color block and/or semicolon so that the user can just type out email with the keypad. The system will know whether to email or SMS based on whether an email is selected or a mobile phone number.

FIGS. 36A-D illustrate examples of LifePower user interfaces for the community-specific and personalized nutrition and activity planning system. The system can be integrated with Facebook or other social networking system and may have unique badge designs and unique ways of sorting what's most important to look at regarding nutrients to act on daily and weekly (or other time period) level, such as needed nutrients got enough of: green/good job; too much of a healthy nutrient or not enough: stay balanced; too much of a generally unhealthy nutrient (markers of processed foods), in Watch Out, red when too much and thresholds personalized based on Institute of Medicine Guidelines. The user interfaces permit the user to navigate through the various nutritional data.

Figure 37:
FIG. 37 illustrates an example of a mobile coupon/voucher of the community-specific and personalized nutrition and activity planning system.

FIG. 37 illustrates an example of a mobile coupon/voucher of the community-specific and personalized nutrition and activity planning system. The mobile coupon/voucher may be similar to the GoalGetter coupon above, but the system can also generate voucher, now with barcodes (as shown in FIG. 37) that work with Point of Sale systems, including QR, UPC, Data Bar, PDF 147. Each coupongo is specific to a person (name included on it) and to a 16 digit serial code, stored on the personalized nutrition and activity planning unit 46. The voucher/mobile coupon becomes active when a user buys a deal and it can expire (the promotional portion).

Figure 38C:
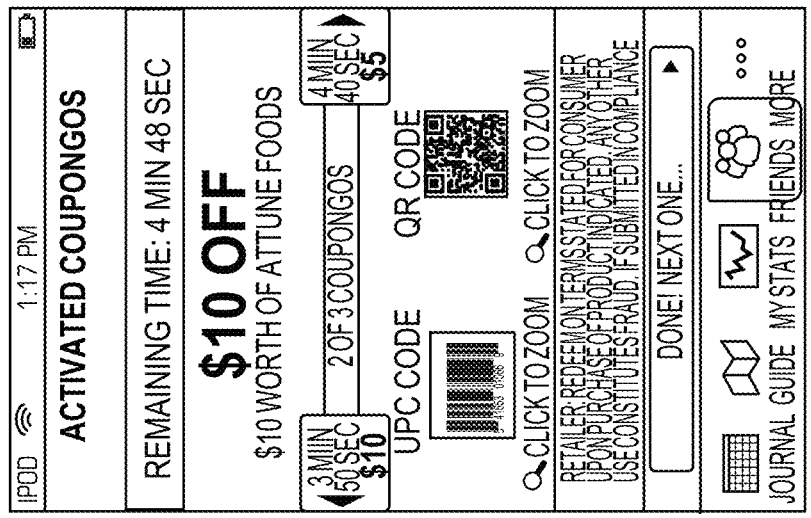
FIGS. 38A-C illustrate examples of the user interface for the computing device app voucher/mobile coupon.
Figure 38B:
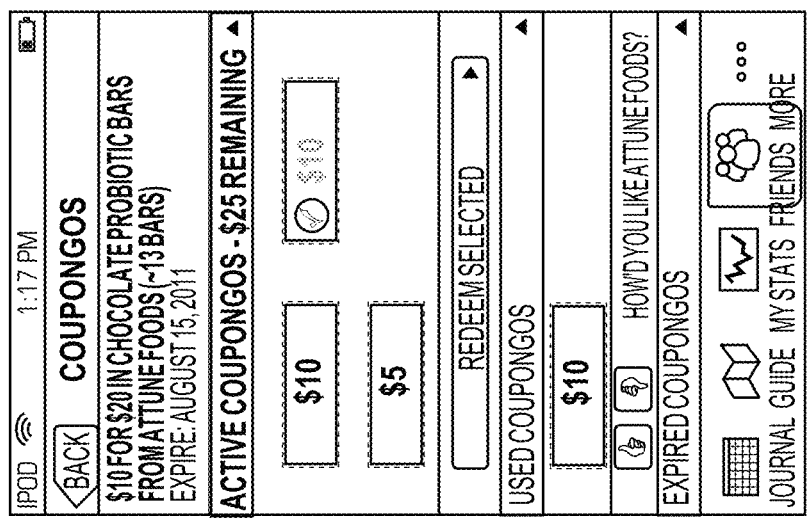
Figure 38A:
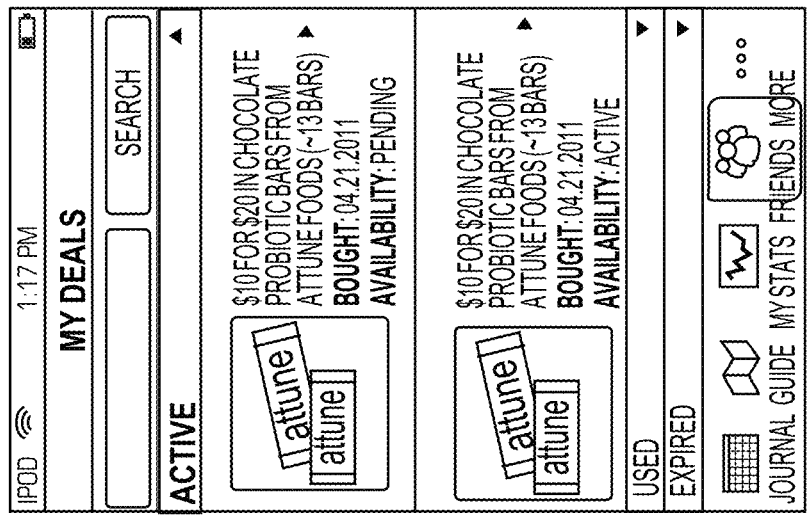

For mobile, the user can select a Deal they bought from their deal list, or Grocery List, (for example as shown in FIG. 38A) and then see the dollar value as ONE OR MORE "Coupongos", that are either still active, have been used or have expired (promotional amount). They can select all the deals and all the coupongos for each deal they want to activate. When they click "Redeem Selected", a timer starts (as shown in FIG. 38C), and a 16 digit unique code is sent to the personalized nutrition and activity planning unit 46 so that the Coupongo will be noted as Used when the timer runs out. The timer gives enough time for the cashier to scan the Coupongo and give the user their discount. The barcode disappears when the timer runs out; only active timers are accepted by cashiers.

The user can thumb slide through multiple activated Coupongo barcodes at once to speed up checkout (as shown for example in FIG. 38C); they can click "Done! Next One" when finished with one to have it be removed from the lineup of barcodes.

Figure 39A:
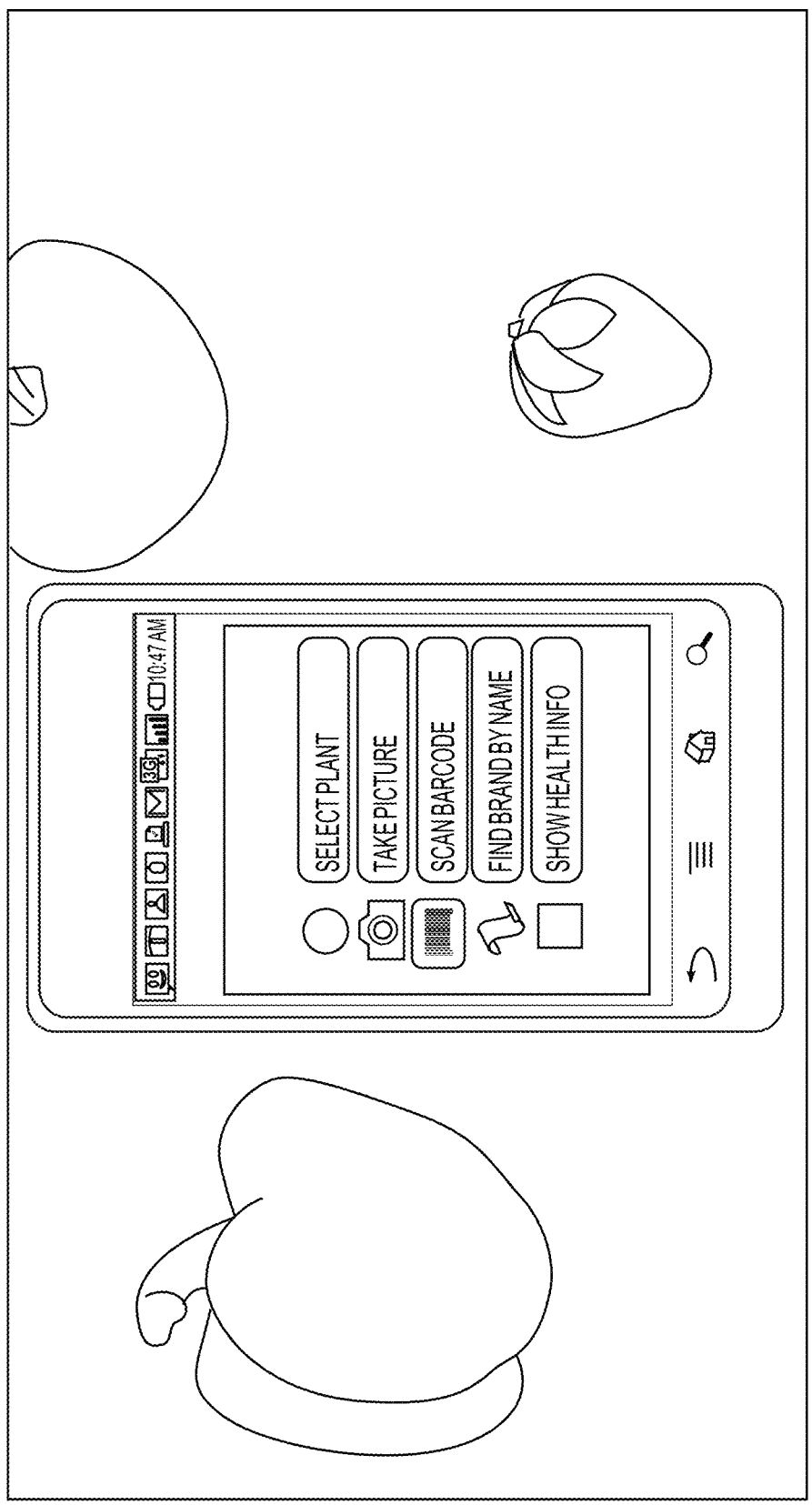
FIGS. 39A-C illustrate an example of geolocation multimodal food item recognition by the computing device app.
Figure 39C:
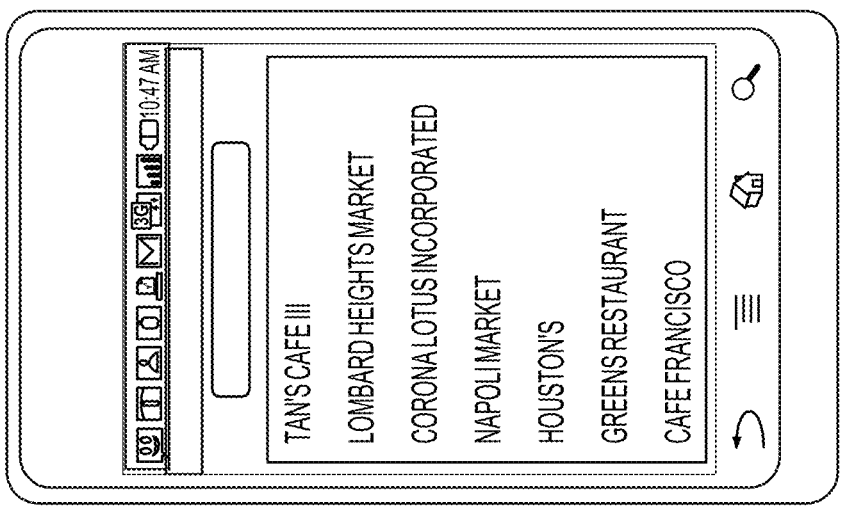
Figure 39B:
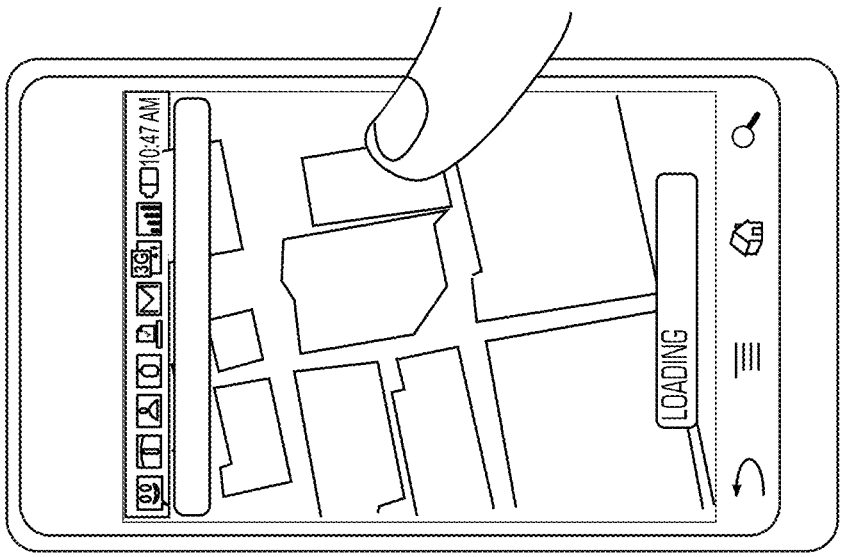

FIGS. 39A-C illustrate an example of geolocation multimodal food item recognition by the computing device app. Using all of the multimodal recognition techniques, a version of the app effectively recognizes fruits and vegetables within top 10 list (90% accuracy within top 5 guess for most common fruits and veggies). FIG. 39A shows the computing device being used to identify the nutrients and the like of a red pepper. FIGS. 39B and 39C shows the geolocating which improves accuracy for predicting food dishes at restaurants (See FIGS. 39B and 39C), by subsetting the possible outcomes (providing a set of foods 'guesses') to the smaller list of that restaurants menu. The geolocation tool may functions like standard 'Check-in' on other apps.

Figure 40B:
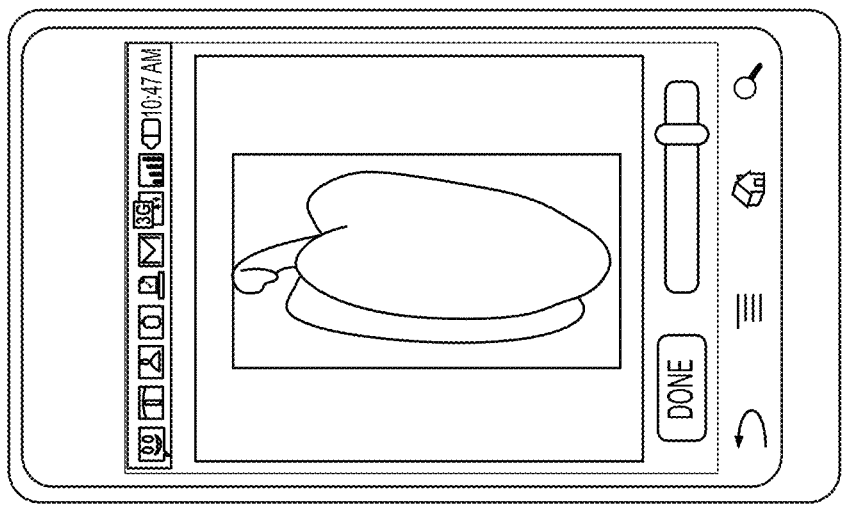
FIGS. 40A-D illustrate an example of visual multimodal food item recognition by the computing device app.
Figure 40A:
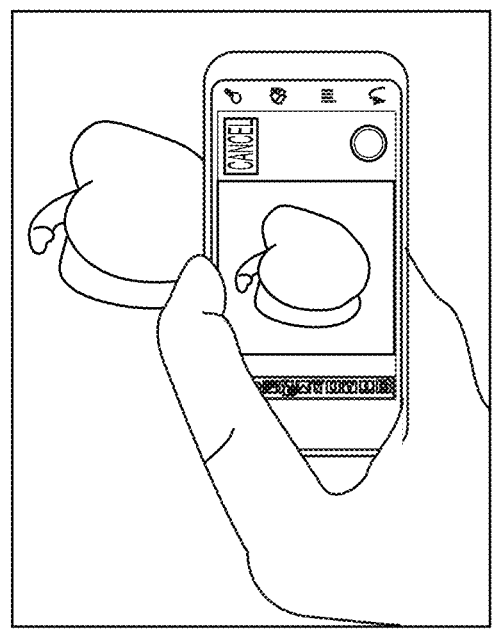
Figure 40C:
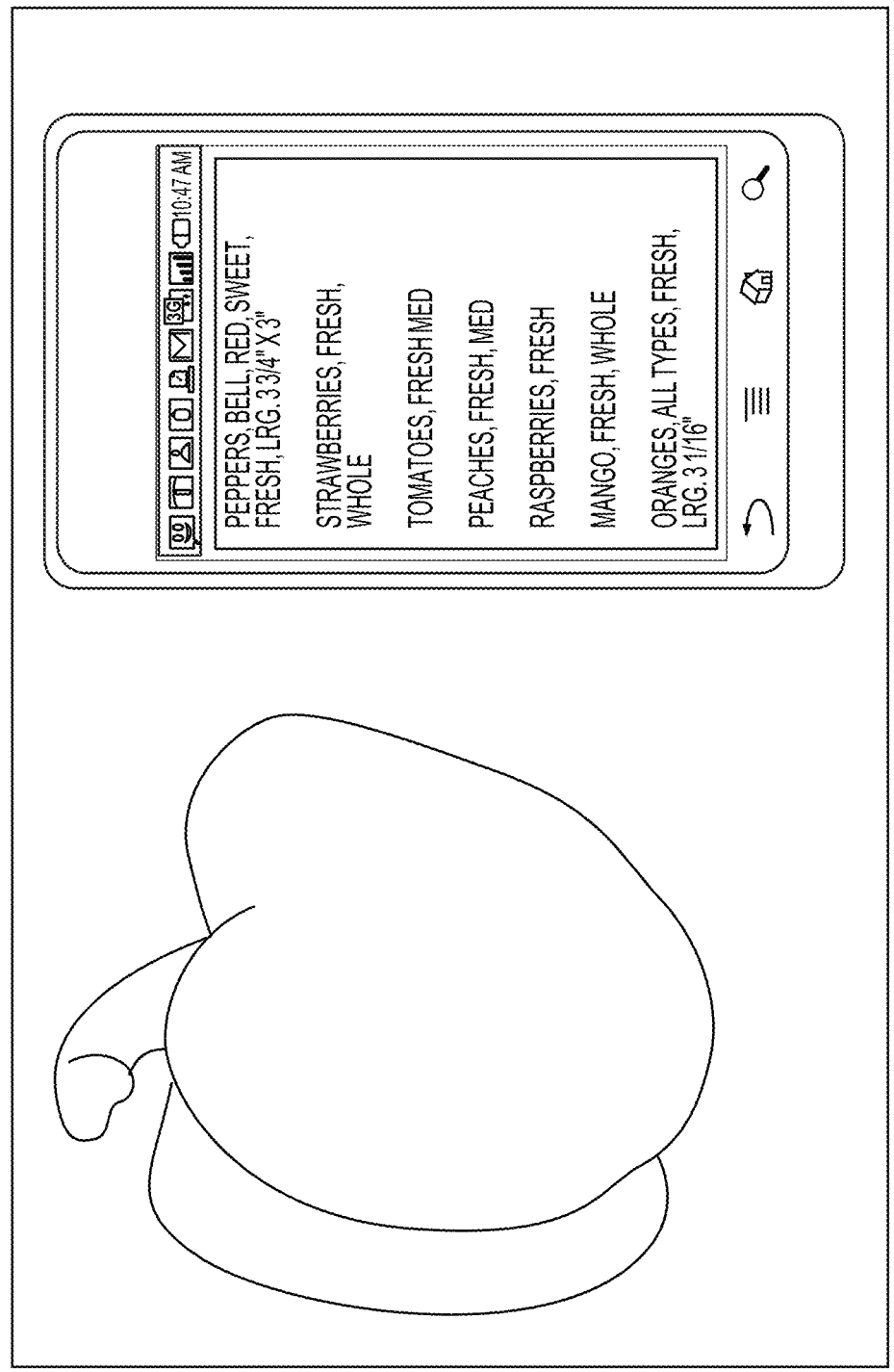
Figure 40D:
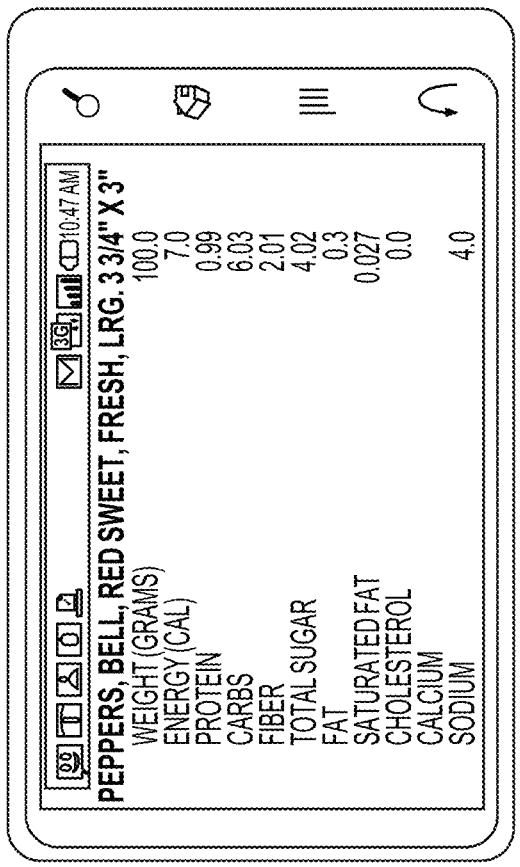

FIGS. 40A-D illustrate an example of visual multimodal food item recognition by the computing device app. The visual recognition (using the camera/image sensor of the computing device to take a picture) (as shown in FIG. 40A) may be used to identify the food item, the portion, nutrient information and the like. The app also allow the user to resize the image of the food item (the bell pepper in this example as shown in FIG. 40B) so that the user can draw (or autodraw) around likely area of interest as was described above. FIG. 40C shows the predicted list of food guesses (the subsetting) based on the captured image. The user interface may also display search suggestions. As shown in FIG. 40D, once the food item has been identified, the app user interface can list identity, portion/size and nutrition info for this vegetable (red pepper) so that the food item can be automatically identified and its nutritional information shown to the user and used by the system for tracking the user's food intake.

Figure 41B:
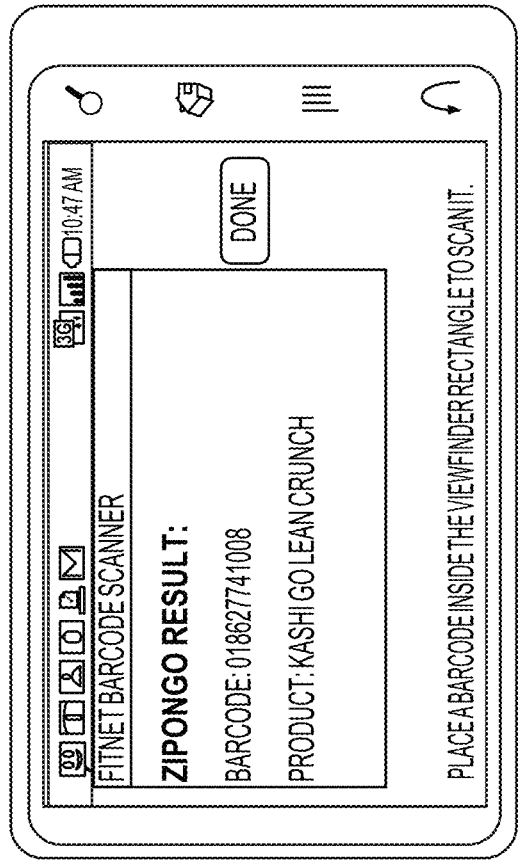
FIG. 41A-B illustrate an example of barcode based multimodal food item recognition by the computing device app.
Figure 41A:
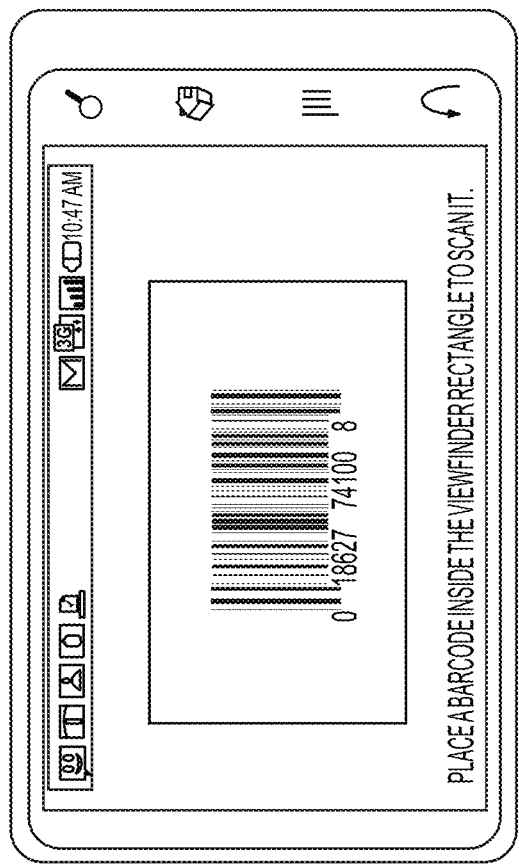

FIG. 41A-B illustrate an example of barcode based multimodal food item recognition by the computing device app. In particular, the UPC code or barcode on a package of a piece of food (another of the multimodal recognition techniques) may be scanned using the computing device to obtain an identification of the food and package information about the food.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A system for nutritional management, comprising:
one or more computing devices;
a nutritional management unit that is capable of being connected to and interacting with each of the one or more computing devices over a link, each of the one or more computing devices communicating data directly to the nutritional management unit; and
the nutritional management unit further comprising a nutritional tracking unit that uses multimodal recognition including image analysis of pixel color and texture and distance of an image of a food to determine the identity, portion size, caloric value and nutritional value of the food from the image, and by using geolocation data, barcode analysis and voice recordings to subset the image analysis search space to the available foods at a particular food venue, and a recommendation unit that delivers personalized recommendations to a user, based on user data, to balance the caloric and nutritional value, wherein the personalized recommendations include physical activity, sleep duration recommendations for the user, recommended recipes, recommended grocery list items and recommended prepared meals from restaurants, and connect such recommendations to actions the user can take in real-time including the digital purchase of a food or activity gear.

2. The system of claim 1, wherein the nutritional tracking unit further comprises a user interface that allows the user to track entries of nutritional planning.

3. The system of claim 2, wherein the entries are one of a meal, an exercise, a sleep time, a mood and a custom item.

4. The system of claim 1, wherein the user data further comprises one or more of stored foods, stored activities, favorite and least favorite foods and activities, restrictions, budget information, transportation preferences, home location, age, gender and wherein the recommendation unit recommends one of a personalized meal and a personalized activity to the user based on the user data.

5. The system of claim 2, wherein the user interface generates a lifemap that displays one or more variables over a period of time for the user based on the user data.

6. The system of claim 5, wherein the one or more variables are one of calories, breakdown of carbohydrate, fat, protein or other nutrients, exercise caloric output, duration, intensity and type, sleep duration and quality, mood score, body weight or fat percentage, and other symptoms, performance outcomes or disease outcomes.

7. The system of claim 1, wherein the multimodal recognition is one of images and image distance from a camera and image analysis of pixel color and texture, and crowdsourced image assessment and barcode analysis and voice recordings and free text and subsetting to menus upon using a Global Positioning System to check into and therefore identify the geolocation of a specific food venue.

8. The system of claim 1, wherein each computing device is one of a smartphone mobile device, a laptop computer, a tablet computer, a body scale, an accelerometer or GPS-based physical activity tracking device, and a sleep tracking device.

9. The system of claim 1, wherein the nutritional tracking unit generates a personalized plan and guide for the user based, in part, on the recommendations.

10. The system of claim 1, wherein the nutritional tracking unit generates a digital food order, following receipt of a recommendation, that is immediately purchasable or is purchasable with a printable voucher or coupon that is redeemable for one of a discounted purchase and a free purchase through any point of sale system by a user of the system.

11. The system of claim 1, wherein the nutritional tracking unit generates a mobile voucher or coupon that is redeemable for one of a discounted purchase and a free purchase through a point of sale system by a user of the system.

12. The system of claim 1, wherein the nutritional tracking unit predicts a risk of future diseases and causes of symptoms of the future diseases.

13. A method for nutritional management, physical activity management, sleep management, weight management and performance management using one or more computing devices and a nutritional management unit that is capable of being connected to and interacting with each of the one or more computing devices over a link, the method comprising:
recognizing, by a nutritional tracking unit of the nutritional management unit, a identity, portion size, caloric value and nutritional value of a food from an image by analysis of pixel color and texture and distance of the image, and by using geolocation data, barcode analysis and voice recordings to subset-the image analysis search space to the available foods at a particular food venue; and
delivering, by a recommendation unit of the nutritional management unit, personalized recommendations to a user, based on user data, to balance the caloric and nutritional value, wherein the personalized recommendations include physical activity and sleep duration recommendations for the user, recommended recipes, recommended grocery list items and recommended prepared meals from restaurants, and connect such recommendations to actions the user can take in real-time including the digital purchase of a food or activity gear.

14. The method of claim 13 further comprising generating, by the nutritional tracking unit, a user interface that allows the user to track entries of nutritional planning.

15. The method of claim 14, wherein the entries are one of a meal, an exercise, a sleep time, a mood and a custom item.

16. The method of claim 13, wherein the multimodal recognition is one of images and image distance from a camera and image analysis of pixel color and texture, and crowdsourced image assessment and barcode analysis and voice recordings and free text and subsetting to menus upon using a Global Positioning System to check into and therefore identify the geolocation of a specific food venue.

17. The method of claim 13, wherein the user data further comprises one or more of stored foods, stored activities, favorite and least favorite foods and activities, restrictions, budget information, transportation preferences, home location, age, gender and wherein recommending one of a meal and an activity to the user further comprises recommending one of a personalized meal and a personalized activity to the user based on the user data.

18. The method of claim 13 further comprising generating a lifemap that displays one or more nutritional variables over a period of time for the user based on the user data.

19. The method of claim 18, wherein the one or more nutritional variables are one of calories, exercize, sleep and mood.

20. The method of claim 13 further comprising generating, by the nutritional tracking unit, a personalized plan guide for the user based, in part, on the recommendations.

21. The method of claim 13 further comprising generating one of a voucher and a mobile coupon that is redeemable by the user of the system.

22. The method of claim 13 further comprising predicting, by the nutritional tracking unit, a risk of future diseases and causes of symptoms based on the user data.

* * * * *